US012623048B1

(12) United States Patent
Tabibian

(10) Patent No.: US 12,623,048 B1
(45) Date of Patent: May 12, 2026

(54) AI-DRIVEN SYSTEM AND METHODS FOR PERSONALIZED VIRTUAL MEDICAL AND SPIRITUAL ADVISOR AVATARS WITH ADAPTIVE THERAPEUTIC AUDIO, BIOMETRIC MONITORING, AND IMMERSIVE AR/VR HEALTHCARE INTERFACES

(71) Applicant: Michael P. Tabibian, Los Angeles, CA (US)

(72) Inventor: Michael P. Tabibian, Los Angeles, CA (US)

( * ) Notice: Subject to any disclaimer, the term of this patent is extended or adjusted under 35 U.S.C. 154(b) by 0 days.

(21) Appl. No.: 19/218,530

(22) Filed: May 26, 2025

Related U.S. Application Data

(60) Provisional application No. 63/786,563, filed on Apr. 10, 2025.

(51) Int. Cl.
A61M 21/02 (2006.01)
G06F 3/01 (2006.01)
(Continued)

(52) U.S. Cl.
CPC ............. A61M 21/02 (2013.01); G06F 3/016 (2013.01); G06T 19/006 (2013.01); G11B 27/34 (2013.01);
(Continued)

(58) Field of Classification Search
CPC .................................................. A61M 21/02
(Continued)

(56) References Cited

U.S. PATENT DOCUMENTS 10,593,423 B2    3/2020  Baldwin
12,383,696 B2 *  8/2025  Poltorak ................ G16H 20/70
(Continued)

FOREIGN PATENT DOCUMENTS

CN        107340865 B      12/2020
CN        117726728 A       3/2024
(Continued)

OTHER PUBLICATIONS

Bandura, A. (1977). Social learning theory. Englewood Cliffs, NJ: Prentice.
(Continued)

*Primary Examiner* — Ruay Ho
(74) *Attorney, Agent, or Firm* — Vedder Price P.C.

(57) ABSTRACT

A computer-implemented system personalizes virtual advisors for immersive healthcare by creating virtual medical and spiritual avatars that resemble trusted authority figures using deepfake technology and multimodal deep neural networks. The virtual medical advisor tailors guidance by analyzing unstructured electronic health record data with natural language processing and BERT-based techniques while adapting its communication based on real-time physiological data from sensors like EEG and photoplethysmography. Concurrently, the virtual spiritual advisor offers faith-based counseling by factoring in user-declared spiritual preferences and sacred text analysis weighted for doctrinal considerations. Additional features include gamification with cryptocurrency tokens or NFTs for health activities, blockchain-based audit trails for HIPAA compliance, and federated learning with differential privacy. The system also employs 3D anatomical simulations to visualize pharmacokinetics and uses adaptive audio treatments in augmented reality with techniques like binaural beats and haptic feed- (Continued)

back, all optimized through reinforcement learning based on historical interactions.

20 Claims, 10 Drawing Sheets

(51) Int. Cl.

| | |
|---|---|
| *G06T 19/00* | (2011.01) |
| *G11B 27/34* | (2006.01) |
| *G16H 40/67* | (2018.01) |
| *H04R 5/033* | (2006.01) |
| *H04S 7/00* | (2006.01) |
| *A61M 21/00* | (2006.01) |

(52) U.S. Cl.
CPC ............. *G16H 40/67* (2018.01); *H04R 5/033* (2013.01); *H04S 7/307* (2013.01); *A61M 2021/0027* (2013.01); *A61M 2021/005* (2013.01); *A61M 2205/3306* (2013.01); *A61M 2205/505* (2013.01); *A61M 2209/088* (2013.01); *A61M 2230/06* (2013.01); *A61M 2230/10* (2013.01); *A61M 2230/65* (2013.01); *G06T 2210/41* (2013.01); *G06T 2210/56* (2013.01); *H04R 2460/13* (2013.01); *H04S 2400/11* (2013.01); *H04S 2400/13* (2013.01)

(58) Field of Classification Search
USPC ........................................................ 706/62
See application file for complete search history.

(56) References Cited

U.S. PATENT DOCUMENTS

| | | | |
|---|---|---|---|
| 12,469,483 B1 | 11/2025 | Tran | |
| 2004/0010418 A1 | 1/2004 | Buonocore et al. | |
| 2015/0196229 A1 | 7/2015 | Old et al. | |
| 2017/0329933 A1 | 11/2017 | Brust et al. | |
| 2019/0201691 A1* | 7/2019 | Poltorak | A61B 5/374 |
| 2019/0282450 A1 | 9/2019 | Lam | |
| 2020/0086078 A1* | 3/2020 | Poltorak | A61N 2/006 |
| 2020/0368491 A1* | 11/2020 | Poltorak | A61N 1/0456 |
| 2021/0041953 A1* | 2/2021 | Poltorak | H04W 4/80 |
| 2021/0390418 A1 | 12/2021 | Mass et al. | |
| 2022/0167857 A1 | 6/2022 | Lin | |
| 2022/0176151 A1 | 6/2022 | Brown | |
| 2022/0225920 A1* | 7/2022 | Read | A61B 5/0042 |
| 2022/0273907 A1* | 9/2022 | Poltorak | A61B 5/378 |
| 2022/0384027 A1 | 12/2022 | Kaleal, III et al. | |
| 2023/0405319 A1 | 12/2023 | Simon et al. | |
| 2024/0296348 A1 | 9/2024 | Neumann | |
| 2024/0361827 A1 | 10/2024 | McNulty et al. | |
| 2024/0420846 A1 | 12/2024 | Hernandez et al. | |
| 2025/0065144 A1 | 2/2025 | Ansari et al. | |
| 2025/0201420 A1 | 6/2025 | Morse et al. | |
| 2025/0210206 A1 | 6/2025 | Ptaszek et al. | |
| 2025/0242167 A1 | 7/2025 | Opitz et al. | |

FOREIGN PATENT DOCUMENTS

| | | |
|---|---|---|
| IN | 2010DEN03462 A | 10/2010 |
| IN | 202141057637 A | 2/2022 |
| WO | 2020041528 A1 | 2/2020 |
| WO | 2024194863 A1 | 9/2024 |

OTHER PUBLICATIONS

Cialdini, R. B. (2009). Influence: Science and practice. Boston: Pearson Education.
Kabat-Zinn, J. (2013). Full catastrophe living: Using the wisdom of your body and mind to face stress, pain, and illness. New York: Bantam Books.
Koenig, H. G. (2012). Spirituality in patient care: Why, how, when, and what. Templeton Foundation Press.
Masters, K. S., & Spielmans, G. I. (2007). Prayer and health: Review, metaanalysis, and research agenda. Journal of Behavioral Medicine, 30(4), 329-338.
Mittelstadt, B. D., Allo, P., Taddeo, M., Wachter, S., & Floridi, L. (2016). The ethics of algorithms: Mapping the debate. Big Data & Society, 3(2).
Norcross, J. C. (2011). Psychotherapy relationships that work: Therapist contributions and responsiveness to patients. Oxford University Press.
Pargament, K. I. (1997). The psychology of religion and coping: Theory, research, practice. Guilford Press.
Pargament, K. I. (2013). Spirituality integrated psychotherapy: Understanding and addressing the sacred. Guilford Press.
Shapiro, S. L. (2009). The integration of mindfulness and psychology.
Riva, G., & Wiederhold, B.K. (2020), The new dawn of virtual reality in health care: Medical simulation and experiential interface, Annual Review of Cyber Therapy and Telemedicine, 18, 3-7.
Li, A., Montaño, Z., Chen, V.J., & Gold, J.I. (2011), Virtual reality and pain management: Current trends and future directions, Pain Management, 1(2), 147-157.-61.
Garrett, B., Taverner, T., & McDade, P. (2017), Virtual reality as an adjunct home therapy in chronic pain management, JMIR Medical Informatics, 5(2), e11.
Fodor, L.A., Coteţ, C.D., Cuijpers, P., et al. (2018), The efficacy of VRbased interventions for symptoms of anxiety and depression, Journal of Affective Disorders, 239, 142-149.
Naghdi, L., Ahonen, H., Macario, P., & Bartel, L. (2015), The effect of low frequency sound stimulation on fibromyalgia patients, Pain Research and Management, 20(1), e21-e27. DOI: 10.1155/2015/375174.
Dos Santos, A.C., De Abreu, M.S., De Mello, G.P., et al. (2023), Solfeggiofrequency music exposure reverses cognitive deficits in zebrafish, Behavioural Brain Research, 450, 114461. DOI: 10.1016/j.bbr.2023.114461 [0518].
Vincent, C., Eberts, M., Naik, T., et al. (2021), Provider experiences of virtual reality in clinical treatment, PLOS ONE, 16(10), e0259364. DOI: 10.1371/journal.pone.0259364.
Merzenich, M.M., et al. (1983), Somatosensory cortical map changes following digit amputation, Journal of Comparative Neurology, 224(4), 591-605.
Doidge, N. (2007), The Brain That Changes Itself, Penguin Books.
Padmanabhan, R., Ali, A., Longe, O., et al. (2005), Binaural beat effects on EEG and heart rate, Applied Psychophysiology and Biofeedback, 30(3), 291-300. Journal of C.
Deci, E. L., & Ryan, R. M. (1985). Intrinsic motivation and self-determination in human behavior. Plenum.
Landers, R. N. (2014). Developing a theory of gamified learning: Linking serious games and gamification of learning. Simulation & Gaming, 45(6), 752-768.
Locke, E. A., & Latham, G. P. (2002). A theory of goal setting & task performance. Prentice-Hall, Inc.
Nakamoto, S. (2008). Bitcoin: A peer-to-peer electronic cash system.
Lipton, B. H. (2005). The biology of belief: Unleashing the power of consciousness, matter, and miracles. Hay House.
Pert, C. B. (1997). Molecules of emotion: The science behind mind-body medicine. Scribner.
Trappl, R. (Ed.). (2016). A construction manual for robots' ethical systems: Why they are needed and how they could be built. Springer.
Weinberger, J. (1992). Common processes underlying psychotherapy. Clinical Psychology Review, 12(5), 479-498.
Wood, J. V., Perunovic, W. Q. E., & Lee, J. W. (2009). Positive Self Statements: PowerOthers. Psychological Science, 20(7), 860-866.
Marco Ruggiero, Chanting of Nam-Myoho-Renge-Kyo in the Context of the Buddhist Liturgy of Nichiren Shoshu: Study of Sound Frequencies, Brain Activity, and Microbial Metabolism, 14 pages, Preprints.org, Aug. 7, 2024, <https://www.preprints.org/manuscript/202407.0236>.

(56)        References Cited

OTHER PUBLICATIONS

Micah J. Sheller, et al., Federated learning in medicine: facilitating multi-institutional collaborations without sharing patient data, Scientific Reports, 10, Article No. 12598, Jul. 28, 2020, 12 pages, Open access <https://doi.org/10.1038/s41598-020-69250-1>.

Ran Zhang, et al., EEG-based real-time BCI system using drones for attention visualization, Computer Methods in Biomechanics and Biomedical Engineering, Feb. 13, 2025, 11 pages, Taylor & Francis Online <https://doi.org/10.1080/10255842.2025.2459272>.

Robb, T.J., Liu, Y., Woodhouse, B. et al. Blending space and time to talk about cancer in extended reality. npj Digit. Med. 7, 261 ( 2024). https://doi.org/10.1038/s417 46-024-01262-x (Year: 2024).

Ceva. (Feb. 12, 2025). Imus in virtual reality applications. https://www.ceva-ip.com/blog/how-imus-are-used-in-vr-applications/ ( Year: 2025).

Cannet, F., Sequera, C., Veloso, P. M., El Kaoutari, A., Methia, M., Richelme, S., Kaya, M., Chemi, A., Dupont, M., Borg, J.-P., Morel, C., Boursier, Y., & Maina, F. (Feb. 20, 2025). Tracing specificity of immune landscape remodeling associated with distinct anticancer treatments. iScience. (Year: 2025).

Lee, S., Kim, S.-P., Yoon, C., Seomoon, E., Yang, T., & Lee, T. (2018) (n.d.). Neural correlates of anxiety induced by environmental events during driving I IEEE conference publication I IEEE Xplore. https://ieeexplore.ieee.org/documenU8650325/ (Year: 2018).

Lin, K., Mohan, V., Ma, Y., Lin, B., Hwang, P., Gopi, P., & Kushida, C. (Apr. 30, 2025). Use of customized binaural beats for the treatment of chronic insomnia. Journal of Sleep Medicine. https://www.e-jsm.org/journal/view.php?number=410 (Year: 2025).

Choi, K. Y. (May 11, 2021 ). Project Overview a Aspire: Clippable, mobile pneumatic-haptic device for breathing rate regulation via personalizable tactile feedback. MIT Media Lab. https://web.archive.org/web/20210511105747/https://www.media.mit.edu/projects/ aspire/overview/ (Year: 2021).

Nairuz, T., Sangwoo-Cho, & Lee, J.-H. (Jun. 3, 2024). Photobiomodulation therapy on Brain: Pioneering an innovative approach to revolutionize cognitive dynamics. MDPI. https://www.mdpi.com/2073-4409/13/11/966#:-:text=Abstract,interest%20within%20the% 20medical%20community. (Year: 2024).

Divino.ai—connect with the divine. Wayback Machine. (Apr. 3, 2024). https://web.archive.org/web/20240403195118/https:// www.divino.ai/ (Year: 2024).

Spirituality and religion. Mental Health America. (Apr. 7, 2025). https://mhanational.org/resources/spirituality-and-religion/#:-:text= Religious %20and %20spiritual %20activities %20can , 6%5 D (Year: 2025).

Zhuyue Ma, Li Sun, Yuanyuan Zhang (2025) The role of virtual reality in breast cancer survivors: A scoping review, Preventive Medicine Reports, vol. 53 (Year: 2025).

Chirico, A., Lucidi, F., De Laurentiis, M., Milanese, C., Napoli, A. and Giordano, A. (2016), Virtual Reality in Health System: Beyond Entertainment. A Mini-Review on the Efficacy of VR During Cancer Treatment. J. Cell. Physiol., 231: 275-287. https://doi.org/10.1002/jcp.25117 (Year: 2016).

* cited by examiner

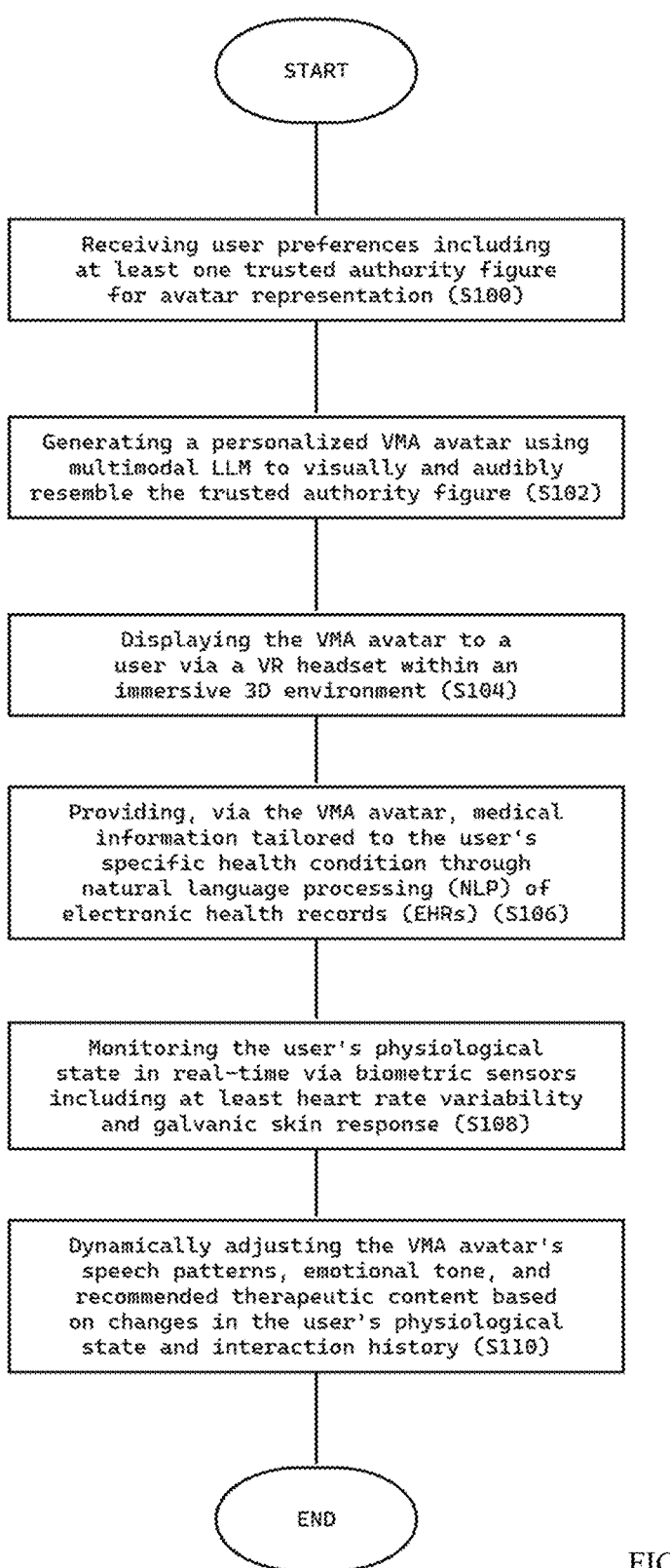

START

Receiving user preferences including
at least one trusted authority figure
for avatar representation (S100)

Generating a personalized VMA avatar using
multimodal LLM to visually and audibly
resemble the trusted authority figure (S102)

Displaying the VMA avatar to a
user via a VR headset within an
immersive 3D environment (S104)

Providing, via the VMA avatar, medical
information tailored to the user's
specific health condition through
natural language processing (NLP) of
electronic health records (EHRs) (S106)

Monitoring the user's physiological
state in real-time via biometric sensors
including at least heart rate variability
and galvanic skin response (S108)

Dynamically adjusting the VMA avatar's
speech patterns, emotional tone, and
recommended therapeutic content based
on changes in the user's physiological
state and interaction history (S110)

END

FIGURE 1

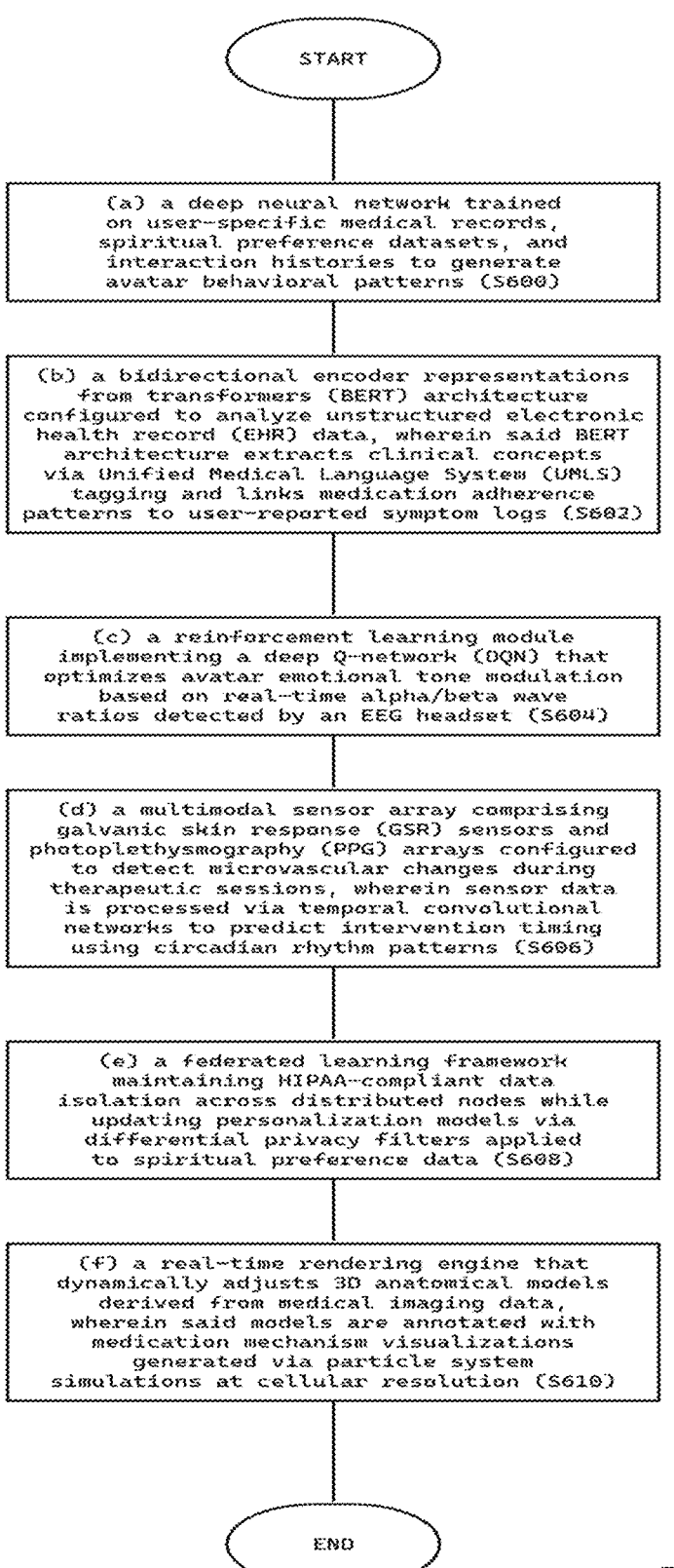

START (a) a deep neural network trained on user-specific medical records, spiritual preference datasets, and interaction histories to generate avatar behavioral patterns (S600)

(b) a bidirectional encoder representations from transformers (BERT) architecture configured to analyze unstructured electronic health record (EHR) data, wherein said BERT architecture extracts clinical concepts via Unified Medical Language System (UMLS) tagging and links medication adherence patterns to user-reported symptom logs (S602)

(c) a reinforcement learning module implementing a deep Q-network (DQN) that optimizes avatar emotional tone modulation based on real-time alpha/beta wave ratios detected by an EEG headset (S604)

(d) a multimodal sensor array comprising galvanic skin response (GSR) sensors and photoplethysmography (PPG) arrays configured to detect microvascular changes during therapeutic sessions, wherein sensor data is processed via temporal convolutional networks to predict intervention timing using circadian rhythm patterns (S606)

(e) a federated learning framework maintaining HIPAA-compliant data isolation across distributed nodes while updating personalization models via differential privacy filters applied to spiritual preference data (S608)

(f) a real-time rendering engine that dynamically adjusts 3D anatomical models derived from medical imaging data, wherein said models are annotated with medication mechanism visualizations generated via particle system simulations at cellular resolution (S610)

END

FIGURE 6

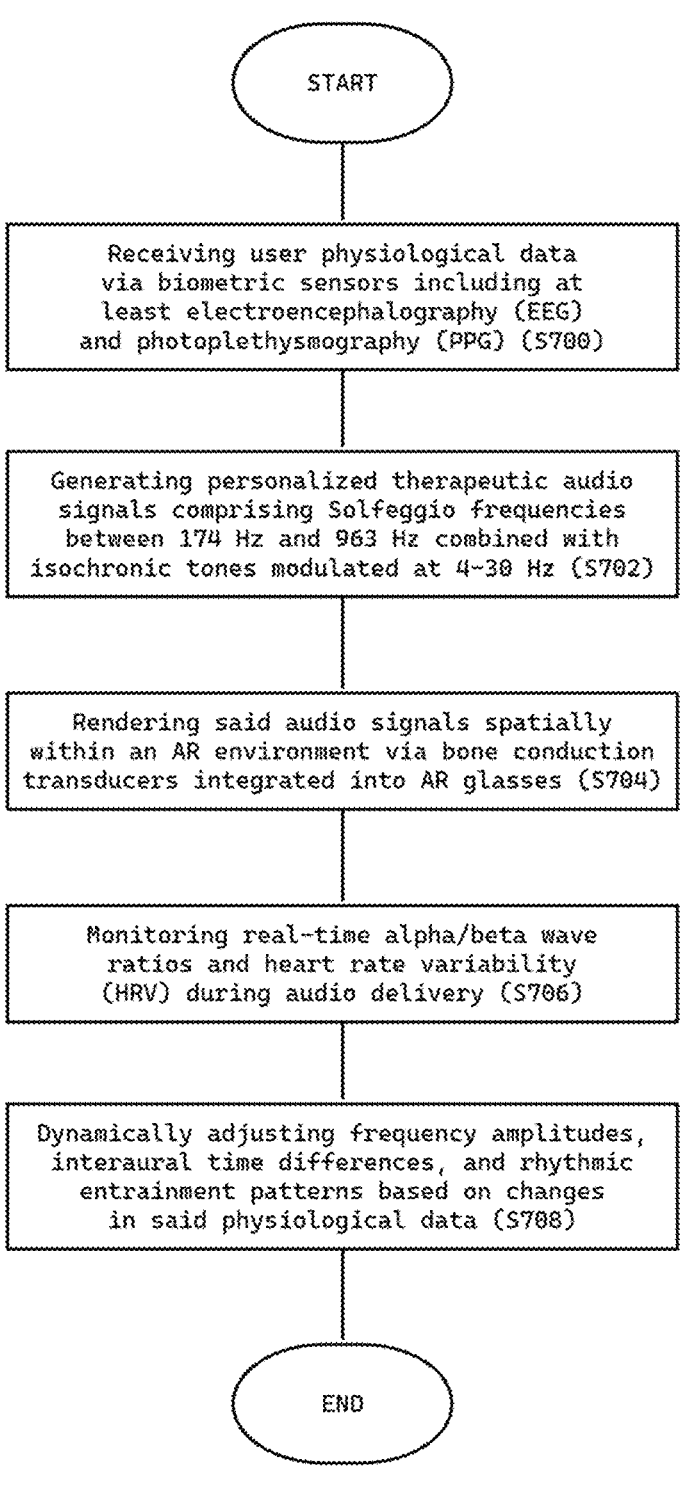

START

Receiving user physiological data
via biometric sensors including at
least electroencephalography (EEG)
and photoplethysmography (PPG) (S700)

Generating personalized therapeutic audio
signals comprising Solfeggio frequencies
between 174 Hz and 963 Hz combined with
isochronic tones modulated at 4-30 Hz (S702)

Rendering said audio signals spatially
within an AR environment via bone conduction
transducers integrated into AR glasses (S704)

Monitoring real-time alpha/beta wave
ratios and heart rate variability
(HRV) during audio delivery (S706)

Dynamically adjusting frequency amplitudes,
interaural time differences, and rhythmic
entrainment patterns based on changes
in said physiological data (S708)

END

FIGURE 7

AI-DRIVEN SYSTEM AND METHODS FOR PERSONALIZED VIRTUAL MEDICAL AND SPIRITUAL ADVISOR AVATARS WITH ADAPTIVE THERAPEUTIC AUDIO, BIOMETRIC MONITORING, AND IMMERSIVE AR/VR HEALTHCARE INTERFACES

The present invention claims priority to Provisional Application 63/786,563 filed Apr. 10, 2025, the content of which is incorporated by reference.

BACKGROUND OF THE INVENTION

Over the past decade, rapid advancements in artificial intelligence, biometric sensing technologies, and immersive digital interfaces have reshaped the landscape of healthcare delivery and wellness management. Concurrent progress in augmented and virtual reality systems has enabled unprecedented levels of user engagement, allowing for the creation of more personalized and effective health interventions that not only address physical ailments but also consider mental and spiritual well-being. These technological strides have led to a paradigm shift toward integrative care models, where real-time feedback and adaptive interfaces facilitate holistic therapeutic experiences. As the convergence of these fields continues to evolve, there is a growing focus on leveraging digital innovations to deliver comprehensive, data-driven, and individualized support in diverse healthcare environments.

SUMMARY OF THE INVENTION

A computer-implemented system is provided for personalized, adaptive virtual advisor functionality within immersive healthcare environments. The methods receive user preferences—including designating trusted authority figures—to generate deepfake-animated virtual medical and spiritual advisor avatars via neural network models and first-order motion algorithms. These avatars deliver tailored medical guidance by analyzing unstructured electronic health records with transformer architectures and offer spiritual content by selecting material from sacred text databases using semantic similarity matching. The system monitors real-time user physiological states via multimodal sensors such as electroencephalography, galvanic skin response, and photoplethysmography, processing these inputs with temporal convolutional networks, Butterworth filters, and reinforcement learning modules to dynamically adjust avatar speech, emotional tone, and therapeutic content. Therapeutic audio, rendered using Solfeggio frequencies and isochronic tones through bone conduction transducers, along with synchronized haptic feedback via wireless protocols, further enhances the user experience. Data privacy and personalization are maintained through federated learning frameworks, differential privacy filters, and secure blockchain ledger recording of interaction data.

In another aspect, a computer-implemented method for generating and operating a virtual medical advisor (VMA) avatar in a virtual reality (VR) healthcare system comprises receiving user preferences including at least one trusted authority figure for avatar representation; generating a personalized VMA avatar using a multimodal large language model (LLM) to visually and audibly resemble the trusted authority figure; displaying the VMA avatar to a user via a VR headset within an immersive 3D environment; providing, via the VMA avatar, medical information tailored to the user's specific health condition through natural language processing (NLP) of electronic health records (EHRs); monitoring the user's physiological state in real-time via biometric sensors including at least heart rate variability and galvanic skin response; and dynamically adjusting the VMA avatar's speech patterns, emotional tone, and recommended therapeutic content based on changes in the user's physiological state and interaction history.

In implementations, the method further comprises one or more of the following: generating therapeutic audio frequencies comprising Solfeggio frequencies between 174 Hz and 963 Hz, synchronized with the VMA avatar's speech output; using deepfake technology with a first-order motion model to animate the VMA avatar's facial expressions based on real-time speech synthesis; implementing a gamification system that awards cryptocurrency tokens for user completion of VMA-prescribed health activities, wherein the cryptocurrency tokens are redeemable for premium VR content or real-world medical services through smart contract verification; analyzing unstructured clinical notes from the EHRs using bidirectional encoder representations from transformers (BERT) architecture; integrating a virtual spiritual advisor (VSA) avatar that provides faith-based counseling complementary to the VMA avatar's medical guidance, wherein the VSA avatar adapts its teachings based on the user's self-identified religious affiliation stored in a spiritual profile database; including biometric sensors such as an EEG headset measuring alpha/beta wave ratios to detect anxiety states, wherein the VMA avatar initiates breathing exercises when alpha wave dominance falls below a predetermined threshold; rendering 3D anatomical models derived from the user's medical imaging data, annotated by the VMA avatar during treatment explanations, wherein the anatomical models visually demonstrate medication mechanisms at cellular resolution using particle system simulations; employing reinforcement learning to optimize content delivery timing based on historical user engagement patterns; generating a blockchain-based audit trail recording all VMA-user interactions for HIPAA-compliant documentation; modulating the VMA avatar's vocal pitch and speech rate inversely proportional to the user's real-time stress levels; triggering haptic feedback through wearable devices synchronized with the VMA avatar's procedural demonstrations; cross-referencing medication databases to visually highlight potential drug interactions in a virtual pharmacy interface; implementing photoplethysmography (PPG) sensors to detect microvascular changes during VMA-guided exposure therapy sessions. The system generates personalized prognostic visualizations using machine learning predictions of treatment outcomes, including probabilistic health trajectories (for example, generating personalized prognostic visualizations using machine learning predictions of treatment outcomes, wherein the visualizations incorporate Monte Carlo simulations showing probabilistic health trajectories based on compliance metrics). The method includes providing a system comprising a VR headset with integrated EEG sensors configured to detect alpha/beta wave ratios, a deepfake processor implementing a first-order motion model to generate facial muscle actuation patterns synchronized with phoneme output, a biometric integration module that receives real-time PPG data from wearable sensors and calculates cardiovascular stress indices using pulse transit time analysis, an AI controller that dynamically adjusts avatar emotional tone through prosody modulation of synthesized speech exceeding ±15% baseline pitch variance and facial action unit intensity scaling based on stress indices, a medical imaging interface that converts DICOM data into deformable 3D organ models and generates particle system visualizations of medication pharmacokinetics, and a haptic feedback subsystem that triggers vibrotactile patterns matching cardiac rhythms during stress states and modulates actuator intensity proportional to galvanic skin response measurements, wherein the system improves VR headset power efficiency by 18-22% through adaptive frame rate reduction during low-stress states.

In another aspect, a computer-implemented method for generating and operating a virtual medical advisor (VMA) avatar in a virtual reality (VR) healthcare system comprises receiving user preferences including at least one trusted authority figure for avatar representation; generating a personalized VMA avatar using deepfake technology to visually and audibly resemble the trusted authority figure; displaying the VMA avatar to a user via a VR headset within an immersive 3D environment; providing, via the VMA avatar, medical information tailored to the user's specific health condition through natural language processing (NLP) of electronic health records (EHRs); monitoring the user's physiological state in real-time via biometric sensors including at least heart rate variability and galvanic skin response; and dynamically adjusting the VMA avatar's speech patterns, emotional tone, and recommended therapeutic content based on changes in the user's physiological state and interaction history.

In a further aspect, a computer-implemented method for AI-driven personalization of virtual medical advisor (VMA) and virtual spiritual advisor (VSA) avatars in a virtual reality (VR) healthcare system comprises receiving user-specific data comprising medical records, spiritual preferences, and interaction history; generating personalized VMA and VSA avatars using deep neural networks trained on user-selected authority figures and behavioral patterns; providing, via the VMA avatar, medical guidance tailored through BERT analysis of unstructured EHR data; delivering, via the VSA avatar, spiritual content dynamically selected from sacred text databases using semantic similarity matching to user-declared beliefs; monitoring real-time physiological states via multimodal sensors including EEG headsets and galvanic skin response (GSR) sensors; and adaptively modifying avatar behaviors, content delivery timing, and environmental parameters using reinforcement learning based on user engagement metrics and biometric feedback.

The method further comprises one or more of the following: identifying medication adherence patterns by cross-referencing prescription records with user-reported symptom logs; implementing a temporal convolutional network to predict optimal intervention timing based on historical circadian rhythm data; employing semantic similarity matching using cosine similarity calculations between user spiritual goals and annotated scriptural passages; generating explainable AI visualizations showing feature importance weights for medical recommendations; utilizing a deep Q-network (DQN) to optimize avatar emotional tone modulation relative to real-time alpha/beta wave ratios; integrating federated learning across multiple user nodes to update personalization models while maintaining HIPAA-compliant data isolation; adapting VSA avatar parable selection frequency based on sentiment analysis of user prayer journal entries; implementing blockchain-anchored audit trails for all AI recommendation changes using smart contract verification; including multimodal sensors such as PPG arrays configured to detect microvascular changes during guided meditation sessions; generating synthetic training data via generative adversarial networks (GANs) to address rare medical condition representation gaps; cross-referencing drug interaction databases using attention mechanisms to highlight contraindications in real-time dialogues; implementing differential privacy filters on spiritual preference data during federated model updates; rewarding the AI agent for maintaining user heart rate variability (HRV) within therapeutic ranges. The method includes knowledge graph embeddings to link medical concepts with spiritual analogies (for example, deploying knowledge graph embeddings to link medical concepts with relevant spiritual analogies during joint VMA-VSA sessions). The method also includes augmenting BERT analysis with clinical concept recognition (CUI) tagging from UMLS ontologies. The method generates counterfactual explanations for declined treatment option recommendations, wherein the explanations provide alternative scenarios for treatment acceptance (for example, implementing counterfactual explanation generators for declined treatment option recommendations). The method includes incorporating denominational doctrinal weightings when selecting interfaith content; optimizing avatar gaze patterns using inverse reinforcement learning from recorded clinician-patient interactions; and dynamically adjusting Solfeggio frequency amplitudes inversely proportional to detected stress biomarkers.

In another aspect, a computer-implemented system for AI-driven personalization of virtual medical advisor (VMA) and virtual spiritual advisor (VSA) avatars in a virtual reality (VR) healthcare environment comprises: a deep neural network trained on user-specific medical records, spiritual preference datasets, and interaction histories to generate avatar behavioral patterns; a BERT architecture configured to analyze unstructured EHR data, wherein said BERT architecture extracts clinical concepts via UMLS tagging and links medication adherence patterns to user-reported symptom logs; a reinforcement learning module implementing a DQN that optimizes avatar emotional tone modulation based on real-time alpha/beta wave ratios detected by an EEG headset; a multimodal sensor array comprising GSR sensors and PPG arrays configured to detect microvascular changes during therapeutic sessions, wherein sensor data is processed via temporal convolutional networks to predict intervention timing using circadian rhythm patterns; a federated learning framework maintaining HIPAA-compliant data isolation across distributed nodes while updating personalization models via differential privacy filters applied to spiritual preference data; and a real-time rendering engine that dynamically adjusts 3D anatomical models derived from medical imaging data, wherein said models are annotated with medication mechanism visualizations generated via particle system simulations at cellular resolution.

In a further aspect, a computer-implemented method for administering adaptive therapeutic audio treatment in an augmented reality (AR) healthcare system comprises receiving user physiological data via biometric sensors including at least EEG and PPG; generating personalized therapeutic audio signals comprising Solfeggio frequencies between 174 Hz and 963 Hz combined with isochronic tones modulated at 4-30 Hz; rendering said audio signals spatially within an AR environment via bone conduction transducers integrated into AR glasses; monitoring real-time alpha/beta wave ratios and heart rate variability (HRV) during audio delivery; and dynamically adjusting frequency amplitudes, interaural time differences, and rhythmic entrainment patterns based on changes in said physiological data.

The method further comprises one or more of the following. The system generates binaural beats by delivering audio tones with slightly different frequencies to each ear to create dichotic auditory stimulation for neural entrainment (for example, incorporating binaural beats with carrier frequencies between 200-900 Hz to generate third-party neural entrainment effects via dichotic auditory stimulation); overlaying visual neurofeedback indicators in the AR field-of-view that pulse synchronously with dominant EEG frequency bands; dynamically selecting Solfeggio frequencies from a prioritized queue based on GSR measurements correlated with emotional valence classifications; predicting optimal audio parameter adjustments using a convolutional neural network based on historical engagement patterns and real-time pupillometry data; contextualizing audio therapy through 3D visualizations of neural oscillatory activity mapped to corresponding treatment frequencies; triggering haptic feedback patterns in wearable devices phase-locked to theta (4-8 Hz) and gamma (30-100 Hz) brainwave synchronization events; dynamically modulating isochronic tones to maintain a 1:2 phase relationship with dominant respiratory sinus arrhythmia rhythms; integrating therapeutic audio with AR-guided mindfulness exercises, wherein spatialized voice prompts adapt cadence inversely proportional to real-time cortisol level estimates; cross-referencing a pharmaceutical database to audibly highlight potential interactions between current medications and specific frequency ranges; generating blockchain-anchored treatment logs recording all audio parameter adjustments and associated biometric responses for regulatory compliance; implementing beamforming techniques in AR glasses to isolate therapeutic audio signals from environmental noise exceeding 65 dB SPL; modulating interaural level differences to create virtual sound source movements synchronized with guided visual focus exercises; implementing differential privacy filters on raw EEG data during federated learning updates to audio personalization models; rendering real-time audiographic representations of autonomic nervous system balance using particle systems responsive to HRV metrics; awarding NFTs for achieving sustained gamma wave coherence during therapeutic sessions; incorporating stochastic resonance patterns calibrated to enhance signal detection in auditory processing pathways; integrating the therapeutic audio with AR-exposure therapy scenarios, dynamically adjusting soundscape complexity based on amygdala reactivity predictions; and implementing a closed-loop reinforcement learning architecture optimizing reward signals based on long-term neuroplasticity biomarkers. The system infers user cortisol level estimates from vocal pitch instability analysis and predicts amygdala reactivity from neural activity measurements derived from EEG data.

A computer-implemented method for operating a virtual spiritual advisor (VSA) system comprises receiving spiritual preference data comprising at least one user-selected spiritual archetype through a graphical user interface; generating a deepfake-animated VSA avatar in real-time using a graphics processing unit (GPU) implementing first-order motion models on reference images stored in non-transitory memory; outputting therapeutic audio frequencies between 174 Hz and 963 Hz through bone conduction headphones while simultaneously displaying the VSA avatar via a virtual reality headset; processing EEG signals through Butterworth filters to detect alpha/beta wave ratios below 0.8 using a biosignal processing pipeline; modulating the VSA avatar's vocal tract parameters through a Griffin-Lim vocoder based on heart rate variability metrics derived from PPG sensor data; synchronizing haptic feedback patterns in a wearable vest with guided meditation sequences using IEEE 15.4 wireless protocols; and recording interaction timestamps and spiritual intervention types in a blockchain ledger using SHA-256 hashing.

The method further comprises one or more of the following: training a BERT model on tokenized sacred texts using byte-pair encoding with 512-token context windows; utilizing facial landmark detection with 68-point facial mesh warping for deepfake animation; implementing a two-phase reinforcement learning process comprising pre-training on historical interaction data and fine-tuning through proximal policy optimization (PPO) with human advisor feedback; including isochronic tones modulated at 10 Hz delta wave patterns in therapeutic audio frequencies; converting unstructured spiritual journal entries into vector embeddings using paragraph-to-vector (Doc2Vec) algorithms; correlating haptic feedback patterns with real-time galvanic skin response measurements through adaptive threshold triggering; rendering three-dimensional mandala visualizations that animate in synchronization with user breathing patterns detected through thoracic impedance pneumography; implementing a blockchain ledger with proof-of-authority consensus through validator nodes operated by licensed spiritual counselors. The method generates personalized affirmation sequences through Markov chain text generation, wherein denominational doctrinal databases constrain the generated sequences (for example by generating personalized affirmation sequences through Markov chain text generation constrained by denominational doctrinal databases).

In yet another aspect, a computer-implemented method for operating a Virtual True Self Avatar (VTSA) with dynamic voice modulation in a virtual reality (VR) healthcare system, comprising: receiving real-time vocal input from a user via a microphone integrated into a VR headset; analyzing acoustic and paralinguistic vocal parameters of the user's voice using AI algorithms, including pitch variation, speaking rate, and hesitation markers; inferring the user's emotional and physiological state through correlations between vocal parameter deviations and predefined stress/anxiety biomarkers; generating a modulated VTSA voice output by adjusting the analyzed vocal parameters toward a target therapeutic profile while preserving the user's vocal timbre; rendering the modulated VTSA voice through bone conduction transducers in the VR headset to replicate internal voice perception; and synchronizing the VTSA's speech content with therapeutic directives from a Virtual Medical Advisor (VMA) or Virtual Spiritual Advisor (VSA) based on electronic health record analysis and spiritual preference databases.

In implementations, the method further comprises one or more of the following: capturing bone conduction resonance patterns during user speech to enhance voice cloning accuracy through mechanical vibration analysis of cranial structures; employing a bidirectional encoder representations from transformers (BERT) model to correlate vocal pitch instability with cortisol level estimates derived from historical EHR data; integrating photoplethysmography (PPG) sensors to validate inferred stress states through real-time microvascular change detection during VTSA interactions; dynamically adjusting voice modulation parameters when PPG data indicates peripheral vasoconstriction exceeding 15% baseline levels; configuring the target therapeutic profile to include a 7-12% reduction in speaking rate and 20 Hz pitch stabilization to mimic vocal patterns associated with parasympathetic nervous system activation; generating a blockchain-anchored audit trail recording all VTSA voice modulation parameters and correlated biometric responses for HIPAA-compliant documentation; delivering frequency-specific vibrotactile feedback (40-120 Hz) via bone conduction transducers synchronized with stressed phoneme detection to enhance self-regulation awareness; utilizing a generative adversarial network (GAN) to synthesize transitional vocal patterns between the user's current state and target therapeutic profile during multi-session therapy; animating the VTSA avatar's facial expressions in real-time using a first-order motion model driven by emotional valence scores derived from vocal parameter analysis; reducing brow furrow intensity by 18-22% in the VTSA animation when vocal tension markers exceed clinical anxiety thresholds; implementing federated learning across user nodes to update voice modulation models while maintaining differential privacy filters on raw audio data; cross-referencing medication databases to avoid vocal pattern modulation that conflicts with known drug-induced dysphonia side effects; awarding cryptocurrency tokens for user achievement of sustained vocal parameter alignment with therapeutic targets; redeeming tokens for premium VR content through smart contracts verifying biomarker improvement thresholds; generating explainable AI (XAI) visualizations showing causal relationships between specific vocal features and modulated output parameters during post-session reviews; optimizing modulation timing with reinforcement learning based on historical user engagement patterns and EEG-measured alpha/beta wave coherence during feedback reception; incorporating 3D laryngeal models that visually demonstrate optimal vocal fold positioning during VTSA-guided breathing exercises; triggering haptic feedback pulses through wearable devices phase-locked to stressed syllable detection in real-time speech analysis; and implementing counterfactual voice samples demonstrating non-modulated versus modulated outcomes to enhance user understanding of therapeutic goals.

Advantages of one implementation may include one or more of the following:

1. Enhanced Personalization and Adaptive Care:
   Provides personalized medical and spiritual guidance through deepfake-animated virtual advisor avatars generated using neural network models.
   Adapts therapeutic content in real time by incorporating unstructured electronic health record analysis, user preferences, and physiological state monitoring.

2. Holistic Integration of Multimodal Technologies:
   Utilizes a wide range of sensors—including electroencephalography, galvanic skin response, and photoplethysmography—to capture comprehensive, real-time user physiological data.
   Integrates medical guidance with spiritual content by leveraging sacred text databases and semantic similarity matching, addressing multidimensional aspects of well-being.

3. Real-Time Feedback and Dynamic Interaction:
   Uses temporal convolutional networks, Butterworth filters, and reinforcement learning modules to analyze user responses and dynamically adjust avatar speech, emotional tone, and content delivery.
   Enhances interactivity through synchronized haptic feedback and therapeutic audio, incorporating Solfeggio frequencies and isochronic tones delivered via bone conduction transducers.

4. Data Security and Privacy:
   Implements federated learning frameworks and differential privacy techniques to protect user-specific data and ensure personalization without compromising privacy.
   Records interaction data on a secure blockchain ledger, providing an immutable audit trail and further enhancing trust.

5. Increased User Engagement and Immersive Experience:
   Leverages augmented and virtual reality systems to create an immersive healthcare environment that increases user engagement and supports sustained therapeutic interventions.
   Offers the ability to designate trusted authority figures for generating avatars, fostering a psychologically comforting and familiar interaction experience.

6. Scalability and Integration in Diverse Healthcare Settings:
   The system's computer-implemented architecture and modular design facilitate integration into various healthcare environments, from clinical settings to personalized home care.
   The adaptive nature of the virtual advisor supports a wide range of applications, from routine wellness management to more specialized therapeutic interventions.

These advantages underscore one implementation's potential to transform the delivery of healthcare and wellness management by combining innovative AI techniques, immersive digital interfaces, and robust data protection methodologies into a unified, adaptive system.

BRIEF DESCRIPTION OF DRAWINGS

FIG. 1 illustrates a process flowchart for a virtual medical advisor system operation.

FIG. 6 illustrates a flowchart detailing a system for AI-driven personalization of avatars.

FIG. 7 illustrates a flowchart for adjusting therapeutic audio based on biometric data in an AR system.

DETAILED DESCRIPTION OF THE INVENTION

Figure 2:
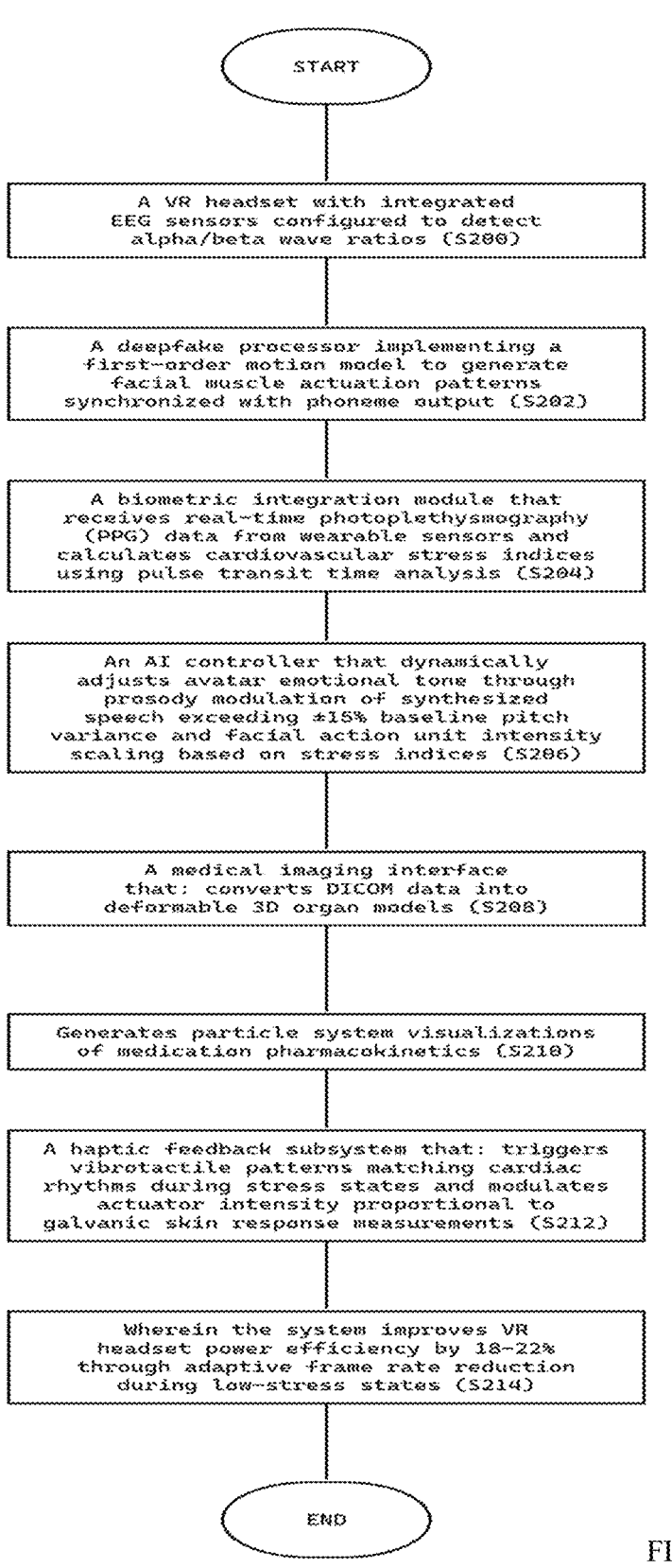
FIG. 2 illustrates a flowchart of a VR healthcare system process involving EEG sensors, biometric modules, AI controllers, and medical imaging interfaces.

The component for receiving user preferences, identified as S100, enables the system to obtain and incorporate data provided by the user, including the selection of at least one trusted authority figure to serve as a basis for avatar representation. This functionality ensures that the system tailors the virtual advisor by incorporating a reference persona approved by the user, thereby laying the groundwork for subsequent personalization processes within immersive healthcare environments.

In one embodiment, the system creates a personalized virtual medical advisor (VMA) avatar that closely resembles a trusted authority figure selected by the user. As described in reference label S102, a multimodal large language model is employed to generate the virtual advisor avatar, wherein the model processes user-selected trusted authority figure data to synthesize visual features including facial structure and dynamic expressions, and auditory features including voice tone and inflection, to create an avatar that visually and audibly resembles the trusted authority figure. The model synthesizes detailed visual features, such as facial structure and dynamic expressions, along with auditory characteristics including voice tone and inflection, to produce an avatar that mirrors the appearance and vocal patterns of the designated figure. This process ensures that the personalized VMA avatar fosters a sense of familiarity and trust through its visual presentation while also supporting coherent communication by replicating authentic speech nuances.

The system includes functionality for displaying the virtual medical advisor (VMA) avatar to a user via a virtual reality headset within an immersive three-dimensional environment as designated by reference label S104. In this implementation, the VMA avatar, which is developed through advanced deepfake and neural network techniques, is rendered in a lifelike manner, allowing the user to perceive and interact with the avatar in a spatially coherent setting. Deepfake technology is implemented through artificial intelligence, specifically deep learning and neural networks, to create hyper-realistic synthetic media. In one implementation, deepfakes uses generative adversarial networks (GANs), where two neural networks—the generator and the discriminator—work in tandem to refine and perfect the manipulation. The generator produces synthetic content, such as swapping faces in a video or altering a person's voice, while the discriminator evaluates its authenticity, gradually improving the realism through iterative learning. To create a deepfake, vast amounts of real-world data—images or video frames of a person—are processed and fed into a model that learns facial expressions, movements, and unique features. The trained model can then manipulate target footage by seamlessly overlaying another individual's likeness, mimicking every nuance of their expression and speech pattern with eerie accuracy. Autoencoders, another crucial deepfake tool, enable efficient facial mapping by compressing input data, understanding key features, and reconstructing them in a transformed output. The implementation of deepfake technology also involves image-processing techniques, such as face detection, segmentation, and alignment, ensuring that the manipulated media blends seamlessly with its surroundings. Alternative implementations for deepfake technology involve variations in model architecture, training methodologies, and intended applications beyond face-swapping. One approach utilizes Variational Autoencoders (VAEs), which focus on encoding and decoding facial features with greater control over latent space representations, allowing for smoother image transitions and modifications. Another alternative is Diffusion Models, a more recent advancement where images are iteratively refined from noise, enabling ultra-realistic and diverse outputs without adversarial training. Additionally, researchers have explored transformer-based architectures, such as Vision Transformers (ViTs), which process facial attributes differently by leveraging attention mechanisms to enhance manipulation precision. Some implementations focus on reenactment rather than synthesis, where models such as First-Order Motion Models use motion transfer techniques to animate still images based on reference movements, achieving realistic character animations for historical or artistic purposes. Another notable implementation includes voice cloning deepfakes, which rely on advanced speech synthesis models like Tacotron and WaveNet to generate synthetic voices with emotional depth and personalized tonality. Beyond individual media alterations, multimodal deepfakes integrate facial, speech, and gesture synthesis, producing complete digital avatars that can engage in dynamic interactions, a technique commonly applied in virtual assistants and gaming. To refine deepfake detection and control, counter-implementation strategies leverage adversarial perturbations and digital watermarking within synthetic media to distinguish authentic content from manipulated visuals. The immersive environment provided by the mobile device such as a virtual reality headset enables real-time interaction with the avatar, ensuring that medical information and guidance are delivered in a context that is engaging and easily comprehensible. This display process is designed to seamlessly integrate with other system functionalities, facilitating an overall enhanced user experience within the healthcare management framework.

The system receives unstructured electronic health record data and processes it using advanced natural language processing algorithms. The virtual medical advisor avatar utilizes these analyses to extract relevant clinical information and tailor medical guidance specifically to the user's health condition. It ensures that the advice is personalized by correlating extracted clinical concepts from the records with established medical protocols. In doing so, the avatar communicates accurate and condition-specific medical information to the user in a clear and accessible manner.

The system processes real-time biometric data from user-worn sensors, including heart rate variability (HRV) derived from photoplethysmography (PPG) sensors, galvanic skin response (GSR), and alpha/beta wave ratios derived from electroencephalography (EEG) sensors, to determine user physiological and emotional states. Another embodiment continuously evaluates the user's physiological state by employing biometric sensors that specifically measure heart rate variability and galvanic skin response. The system collects these signals in real time to assess variations in cardiovascular activity and skin conductivity, which are indicative of the user's current stress or relaxation levels. This data is then analyzed to determine whether adjustments to the therapeutic content or the avatar's interactive behavior are warranted, thus ensuring that the system dynamically adapts to the user's immediate physical condition.

The system employs a neural vocoder to synthesize the avatar's voice, and dynamically adjusts vocal parameters of the synthesized voice, including articulation, tempo, and pitch, based on real-time biometric data received from user-worn sensors. In other implementations, the system monitors the user's physiological state using biometric sensors that measure parameters such as heart rate variability and galvanic skin response. Based on the real-time sensor outputs and the history of user interactions, the AI controller dynamically adjusts the virtual medical advisor's speech patterns. Speech synthesis algorithms modulate factors such as articulation, tempo, and pitch to ensure that the avatar's verbal output resonates with the user's current emotional and physiological condition. Simultaneously, the avatar's emotional tone is fine-tuned by analyzing these biometric inputs so that its affective responses are aligned with the user's sensed stress or relaxation levels. In addition, the system selects therapeutic content tailored to the individual by correlating past interaction history with present sensor data, thereby optimizing the relevance and effectiveness of the advice provided. This approach, described in reference label S110, enables a personalized and responsive interaction that adapts continuously to the evolving clinical and emotional needs of the user in an immersive environment.

FIG. 2 illustrates a flowchart of a VR healthcare system process. It begins with a VR headset featuring integrated EEG sensors (S200), which detect alpha/beta wave ratios. A deepfake processor then uses a first-order motion model to generate synchronized facial muscle actuation patterns (S202). Next, a biometric integration module processes real-time photoplethysmography data to calculate cardiovascular stress indices via pulse transit time analysis (S204). Based on the stress indices, an AI controller adjusts avatar emotional tone by modulating synthesized speech prosody and facial action units (S206). A control loop mechanism dynamically adjusts the avatar's emotional tone and speech patterns by mapping user stress indices, derived from biometric data, to avatar parameters including synthesized speech prosody and facial action unit intensity.

The process continues with a medical imaging interface that converts DICOM data into 3D organ models (S208) and generates visualizations of medication pharmacokinetics using particle systems (S210). A haptic feedback subsystem then activates, triggering vibrotactile patterns corresponding to cardiac rhythms and adjusting actuator intensity in accordance with galvanic skin response measurements (S212). Finally, the system boosts VR headset power efficiency by 18-22% through adaptive frame rate reduction during states of reduced stress (S214).

One implementation features a VR headset integrated with EEG sensors specifically configured to detect alpha/beta wave ratios. The integration of these sensors enables real-time monitoring of the user's brainwave activity, allowing the system to gather detailed information on the user's mental state. This data is essential for adapting the virtual environment and avatar interactions to enhance therapeutic outcomes and user engagement.

One implementation includes a deepfake processor operating with a first-order motion model. This processor is responsible for generating facial muscle actuation patterns that are synchronized with phoneme output. This feature is integral in creating accurate and realistic virtual avatar expressions that align with generated speech, enhancing user interaction within immersive environments.

The system includes a biometric integration module tasked with acquiring real-time photoplethysmography (PPG) data from wearable sensors. This module computes cardiovascular stress indices by employing pulse transit time analysis.

The system incorporates a medical imaging interface configured to transform DICOM data into deformable 3D organ models. This interface enables personalized visualization of anatomical structures, enhancing the understanding of medical conditions. By converting standard medical imaging data into interactive 3D models, healthcare providers can better analyze and communicate complex information. This process facilitates more informed decision-making and patient-specific care strategies, utilizing advanced computational techniques to render precise and adaptable anatomical representations.

The system includes functionality to generate particle system visualizations of medication pharmacokinetics. This process involves creating visual representations of how medications interact within the body, allowing users to better understand the effects at a molecular level. Such visualizations can aid in explaining complex pharmacological processes in a clear and engaging manner.

The system generates haptic feedback patterns via wearable devices, wherein the timing and intensity of the haptic feedback are modulated based on real-time biometric data. In one embodiment, the haptic feedback subsystem is designed to deliver vibrotactile patterns that align with cardiac rhythms when stress states are detected. It also adjusts the intensity of these actuators based on measurements from galvanic skin response sensors. This feature enhances user experience by providing appropriate tactile feedback during various emotional or physiological states.

The system optimizes VR headset power efficiency by implementing adaptive frame rate reduction, yielding an improvement of 18-22% during periods identified as states of diminished stress. This is accomplished by dynamically decreasing the frame rate when physiological data indicates decreased stress levels, thereby conserving energy without compromising user experience.

Figure 3:
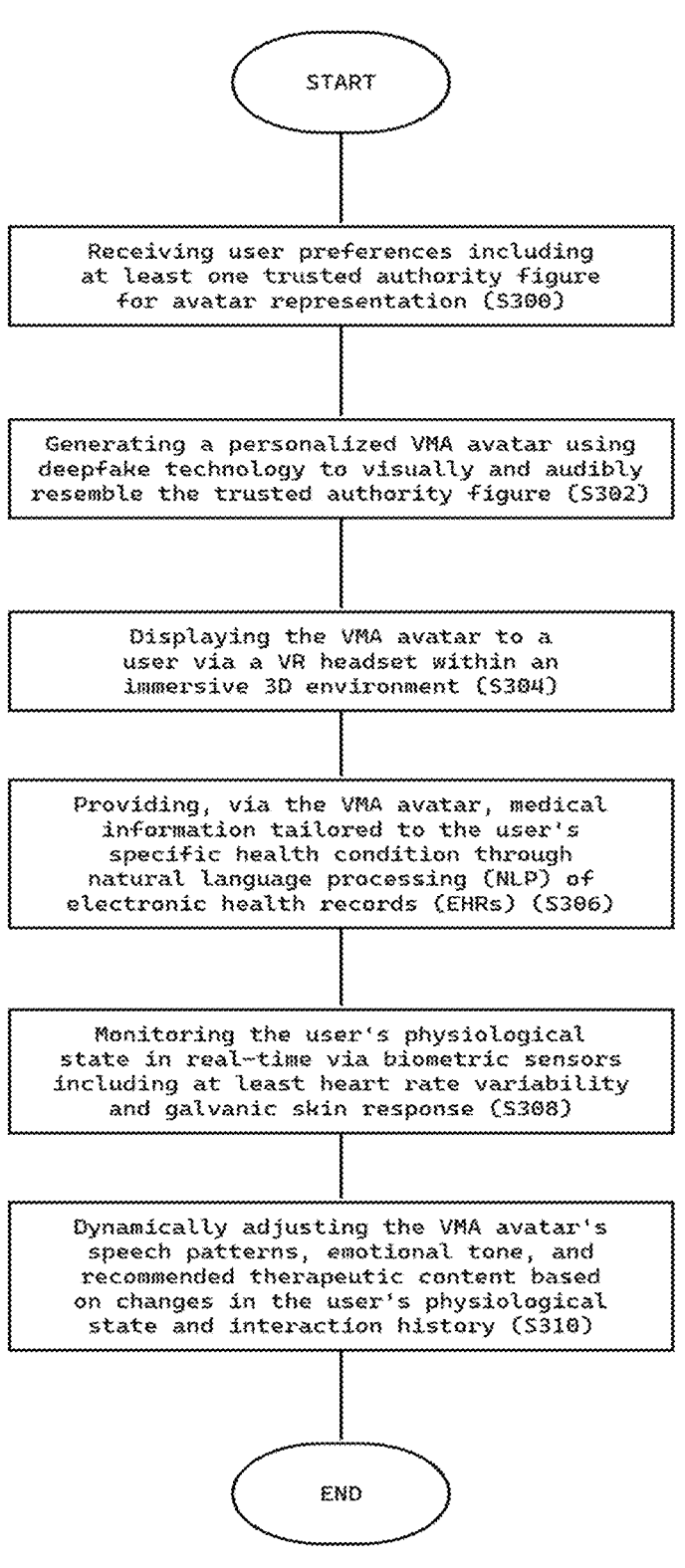
FIG. 3 illustrates a flowchart for operating a virtual medical advisor (VMA) avatar using user preferences, deepfake technology, and physiological monitoring.

FIG. 3 illustrates a flowchart for operating a virtual medical advisor (VMA) avatar. It starts with receiving user preferences, including at least one trusted authority figure for avatar representation (S300). Next, it generates a personalized VMA avatar using deepfake technology to visually and audibly resemble the trusted authority figure (S302). The avatar is then displayed to the user via a VR headset within an immersive 3D environment (S304). Through the VMA avatar, medical information tailored to the user's specific health condition is provided using natural language processing (NLP) of electronic health records (EHRs) (S306). The user's physiological state is monitored in real-time via biometric sensors, including heart rate variability and galvanic skin response (S308). Finally, the VMA avatar's speech patterns, emotional tone, and recommended therapeutic content are dynamically adjusted based on changes in the user's physiological state and interaction history (S310).

The reference label "S310" pertains to the system's ability to dynamically adjust the virtual medical advisor (VMA) avatar's speech patterns, emotional tone, and therapeutic content. This adaptation is based on variations in the user's physiological state and interaction history. The system uses real-time data to ensure that the avatar responds appropriately to the user's changing conditions, optimizing the delivery of personalized therapeutic guidance.

Figure 4:
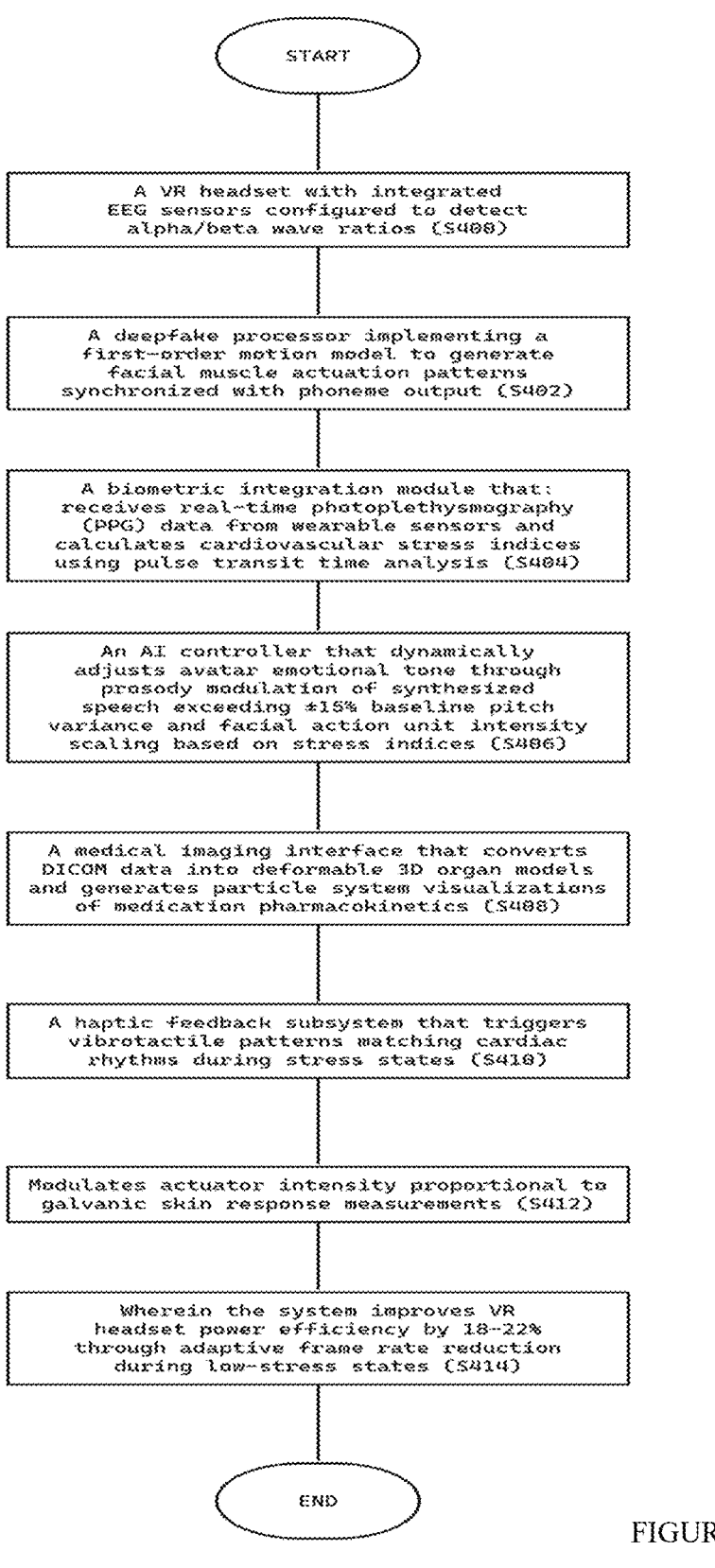
FIG. 4 illustrates a flowchart for a VR system with EEG sensors, deepfake processor, biometric integration, AI controller, medical imaging, and haptic feedback.

FIG. 4 illustrates a flowchart for a VR system that integrates several advanced technologies. It begins with a VR headset equipped with EEG sensors (S400) to detect alpha/beta wave ratios, which informs the operation of a deepfake processor (S402). This processor generates synchronized facial muscle actuation patterns based on phoneme output. The system includes a biometric integration module (S404) that processes real-time photoplethysmography (PPG) data from wearable sensors, calculating cardiovascular stress indices using pulse transit time analysis.

Leverages these indices to dynamically adjust avatar emotional tone, modulating the prosody of synthesized speech and adjusting facial features. The medical imaging interface (S408) transforms DICOM data into deformable 3D organ models, providing visualizations of medication pharmacokinetics. A haptic feedback subsystem (S410) engages vibrotactile patterns that mimic cardiac rhythms during stress states.

The system further modulates actuator intensity based on galvanic skin response measurements (S412) and improves VR headset power efficiency by 18-22% through adaptive frame rate adjustments during reduced-stress conditions (S414), thereby optimizing user experience and energy consumption.

The AI controller is designed to dynamically adjust the emotional tone of the avatar. It accomplishes this by modulating the prosody of synthesized speech, allowing pitch variations of more than plus or minus 15% from the baseline. Additionally, it scales the intensity of facial action units according to stress indices, providing a responsive and emotionally nuanced interaction with the user.

The system includes a mechanism for adjusting the intensity of actuators based on galvanic skin response measurements. This functionality allows for dynamic modulation of feedback intensity in response to physiological indicators, enhancing the adaptability of the system to the user's varying stress levels.

Figure 5:
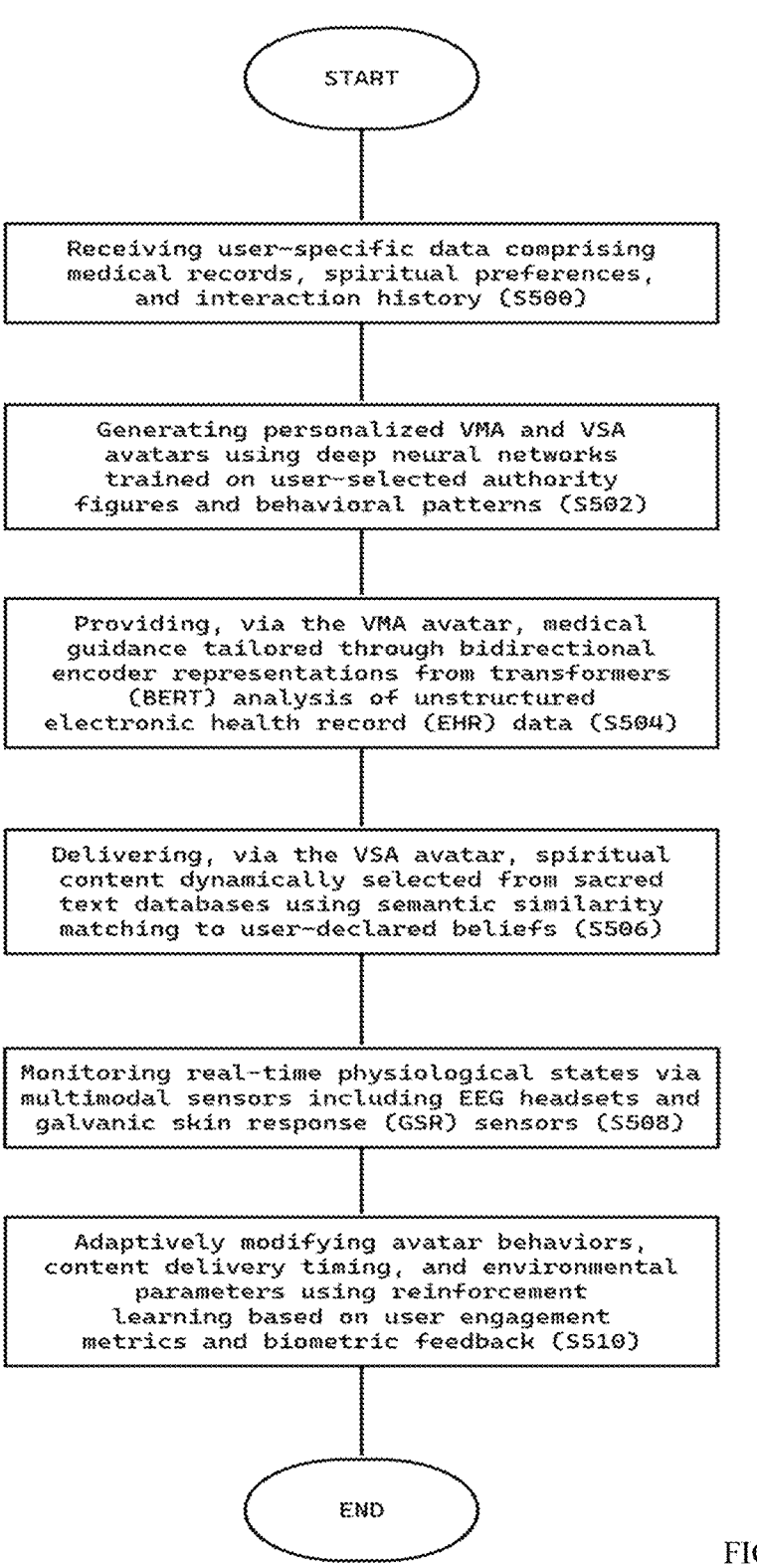
FIG. 5 illustrates a flowchart depicting the process of using personalized virtual medical and spiritual advisor avatars in a VR healthcare system.

FIG. 5 illustrates a flowchart depicting the process of using personalized virtual medical and spiritual advisor avatars in a VR healthcare system. It begins with receiving user-specific data, including medical records, spiritual preferences, and interaction history (S500). This data is used to generate personalized VMA and VSA avatars through deep neural networks trained on user-selected authority figures and behavioral patterns (S502). The VMA avatar provides tailored medical guidance using BERT analysis of unstructured electronic health record data (S504). Concurrently, the VSA avatar delivers spiritual content by dynamically selecting from sacred text databases, using semantic similarity matching to user-declared beliefs (S506). Real-time physiological states are monitored via multimodal sensors, such as EEG headsets and galvanic skin response sensors (S508). The system adaptively modifies avatar behaviors, content delivery timing, and environmental parameters using reinforcement learning based on user engagement metrics and biometric feedback (S510). A reinforcement learning module adaptively modifies avatar behaviors, content delivery timing, and virtual environment parameters based on user engagement metrics and biometric feedback, using a reward function to optimize therapeutic outcomes, wherein observable state variables represent user physiological and emotional states, and the action space comprises avatar behaviors and virtual environment adjustments.

The system facilitates the delivery of spiritual content through a Virtual Spiritual Advisor (VSA) avatar. This content is dynamically chosen from a database of sacred texts using semantic similarity matching techniques. The selection process aligns the content with the user's specified beliefs.

The system leverages reinforcement learning to adaptively modify avatar behaviors, content delivery timing, and environmental parameters. This process is informed by user engagement metrics and biometric feedback, enabling the avatars to dynamically tailor interactions in response to real-time physiological and behavioral data. By continuously analyzing user responses and adjusting the virtual environment accordingly, the system ensures a personalized and responsive user experience.

FIG. 6 illustrates a flowchart for an AI-driven avatar personalization system. It begins with (a) a deep neural network trained using user-specific data, including medical records, spiritual preferences, and interaction histories, to create avatar behavior patterns (S600). The process continues with (b) a BERT architecture that analyzes unstructured EHR data, extracting clinical concepts with UMLS tagging, and links medication adherence to user-reported symptoms (S602). Subsequently, (c) a reinforcement learning module uses a deep Q-network to modulate avatar emotional tone based on EEG-detected alpha/beta wave ratios (S604). The system incorporates (d) a multimodal sensor array with GSR and PPG sensors to detect microvascular changes, processed through temporal convolutional networks to time interventions with circadian rhythms (S606). Additionally, (e) a federated learning framework ensures HIPAA compliance while updating personalization models using differential privacy filters on spiritual data (S608). Finally, (f) a real-time rendering engine adjusts 3D anatomical models from medical imaging data, annotating them with medication visualizations via particle system simulations at cellular resolution (S610).

The system employs a deep neural network (S600) trained using user-specific data, including medical records, spiritual preference datasets, and interaction histories. This training allows the network to generate behavioral patterns for avatars, ensuring they align with individual user profiles and provide personalized interactions.

The system incorporates a bidirectional encoder representations from transformers (BERT) architecture to process unstructured electronic health record (EHR) data. This BERT architecture is engineered to extract clinical concepts using Unified Medical Language System (UMLS) tagging. Furthermore, it is capable of linking medication adherence patterns to user-reported symptom logs, facilitating a comprehensive understanding of the user's health status.

One implementation includes a reinforcement learning module designed to modulate the emotional tone of an avatar dynamically. This module employs a deep Q-network (DQN) to optimize the avatar's emotional expressions by leveraging real-time alpha/beta wave ratio data detected by an EEG headset (S604). This allows the system to adjust the avatar's emotional responses to maintain an appropriate and supportive user interaction experience based on neural feedback.

One implementation incorporates a multimodal sensor array consisting of galvanic skin response (GSR) sensors and photoplethysmography (PPG) arrays. These components are designed to identify microvascular changes during therapeutic sessions. The sensor data undergoes processing through temporal convolutional networks, which enable the prediction of intervention timing by analyzing circadian rhythm patterns.

The system includes a federated learning framework designed to uphold HIPAA-compliant data isolation across distributed nodes. This framework enables the updating of personalization models while ensuring data privacy through the application of differential privacy filters, specifically tailored to manage spiritual preference data. The HIPAA compliance process involves steps to ensure that healthcare organizations and their business associates protect patient health information (PHI) in accordance with federal regulations. The process begins with conducting a risk assessment, where organizations identify potential vulnerabilities in their handling of PHI and assess security risks. Next, they must develop and implement HIPAA policies and procedures, ensuring that day-to-day operations align with the HIPAA Privacy and Security Rules. Organizations are required to designate a HIPAA compliance officer, responsible for overseeing compliance efforts, training staff, and responding to privacy concerns. Employee training is another critical component, ensuring that all personnel understand HIPAA regulations and how to handle PHI securely. Additionally, organizations must establish physical, administrative, and technical safeguards to protect PHI, including access controls, encryption, and secure facility protocols. Regular audits and monitoring help maintain compliance by identifying potential gaps and ensuring corrective actions are taken.

The system includes a real-time rendering engine designed to adjust three-dimensional anatomical models that are derived from medical imaging data. These models are further annotated with visualizations of medication mechanisms. The visualizations are created using particle system simulations at a cellular resolution, ensuring precise and detailed representation of pharmacokinetics.

FIG. 7 illustrates a flowchart for adjusting therapeutic audio based on biometric data in an AR system. Initially, user physiological data is received via biometric sensors, including electroencephalography (EEG) and photoplethysmography (PPG) (S700). Using this data, personalized therapeutic audio signals are generated, incorporating Solfeggio frequencies between 174 Hz and 963 Hz, combined with isochronic tones modulated at 4-30 Hz (S702). These audio signals are then spatially rendered within an AR environment using bone conduction transducers integrated into AR glasses (S704). During audio delivery, real-time monitoring of alpha/beta wave ratios and heart rate variability (HRV) is conducted (S706). Finally, the system dynamically adjusts frequency amplitudes, interaural time differences, and rhythmic entrainment patterns based on changes in the physiological data (S708).

The method involves acquiring user physiological data through biometric sensors, specifically including electroencephalography (EEG) and photoplethysmography (PPG). These sensors facilitate the collection of real-time biometric information, which is essential for monitoring and analyzing the user's physiological states during therapeutic sessions.

The system generates therapeutic audio signals comprising Solfeggio frequencies and isochronic tones, and dynamically adjusts the amplitude of the audio signals and synchronizes the audio signals with avatar speech output. In one implementation, the system generates personalized therapeutic audio signals by incorporating Solfeggio frequencies, which range from 174 Hz to 963 Hz. These frequencies are combined with isochronic tones, modulated between 4 Hz and 30 Hz, to enhance the auditory experience. This combination aims to provide a customized and harmonious sound therapy tailored to the user's needs.

In the step designated as S704, the method involves spatially rendering audio signals within an augmented reality (AR) environment. This is achieved by using bone conduction transducers, which are integrated into AR glasses. These transducers deliver the audio directly through the bones of the skull, allowing the user to experience immersive audio without traditional headphones, enhancing the interaction with the AR environment.

Monitoring real-time alpha/beta wave ratios and heart rate variability (HRV) during audio delivery (S706) involves continuously analyzing the user's brainwave and cardiovascular metrics while therapeutic audio is played. This process utilizes electroencephalography (EEG) sensors to track the balance of alpha and beta brain waves. Simultaneously, heart rate variability is measured to assess the user's stress and relaxation levels. This real-time data collection enables the system to gauge the user's physiological response to the audio, providing insights into emotional and stress states, which are essential for tailoring the therapeutic experience.

The system dynamically adjusts frequency amplitudes, interaural time differences, and rhythmic entrainment patterns based on changes in the user's physiological data. This adjustment is informed by real-time biometric feedback, allowing the audio signals to be fine-tuned to enhance therapeutic outcomes effectively.

Figure 8:
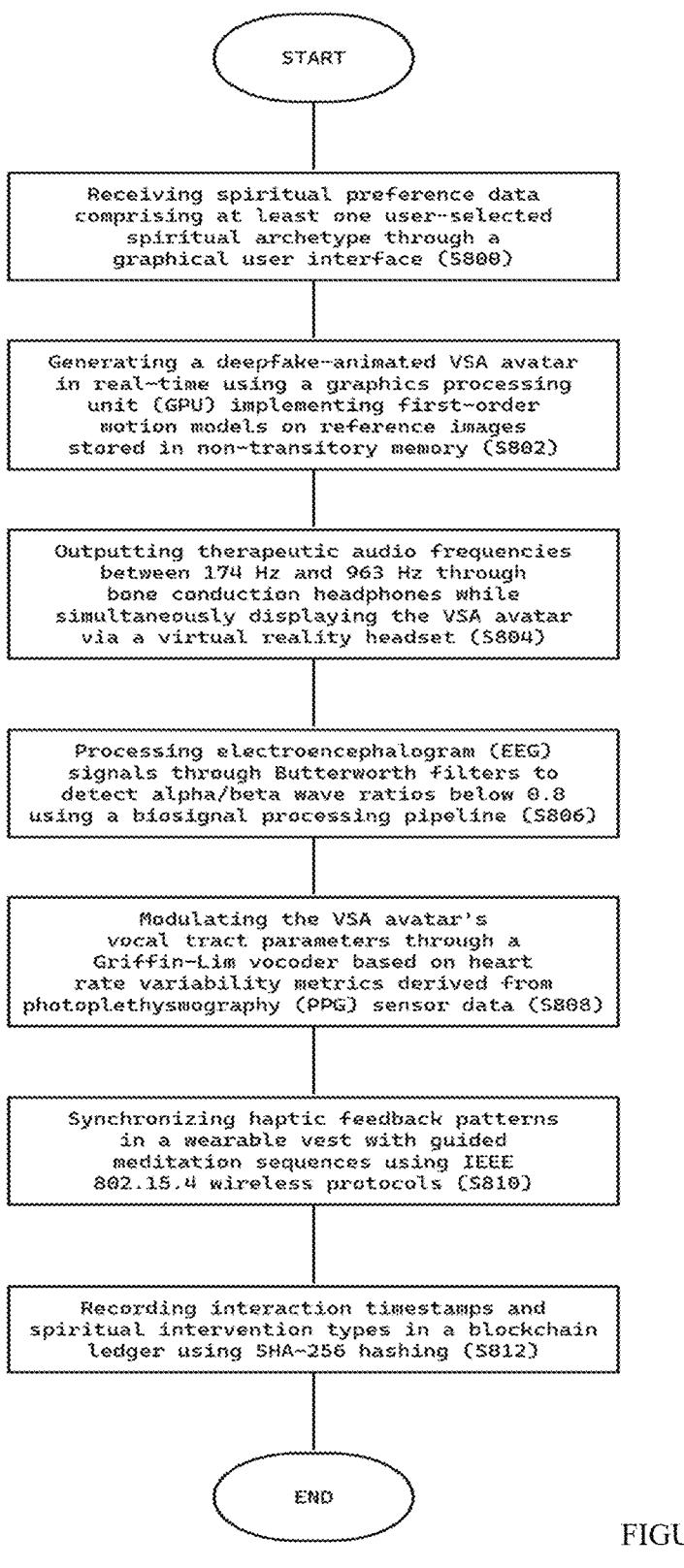
FIG. 8 depicts a flowchart for operating a virtual spiritual advisor (VSA) system using deepfake technology and biometric feedback monitoring.

FIG. 8 illustrates a flowchart depicting the operation of a virtual spiritual advisor (VSA) system. The process begins with receiving spiritual preference data, including at least one user-selected spiritual archetype through a graphical user interface (S800). Subsequently, a deepfake-animated VSA avatar is generated in real-time using a GPU, implementing first-order motion models on reference images stored in non-transitory memory (S802).

The system then outputs therapeutic audio frequencies between 174 Hz and 963 Hz through bone conduction headphones, while simultaneously displaying the VSA avatar via a virtual reality headset (S804). Next, it processes electroencephalogram (EEG) signals through Butterworth filters to detect alpha/beta wave ratios below 0.8 using a biosignal processing pipeline (S806).

Further, the VSA avatar's vocal tract parameters are modulated through a Griffin-Lim vocoder based on heart rate variability metrics derived from photoplethysmography (PPG) sensor data (S808). The flowchart also shows the synchronization of haptic feedback patterns in a wearable vest with guided meditation sequences using IEEE 802.15.4 wireless protocols (S810). Finally, it records interaction timestamps and spiritual intervention types in a blockchain ledger using SHA-256 hashing (S812), concluding the process.

Figure 9:
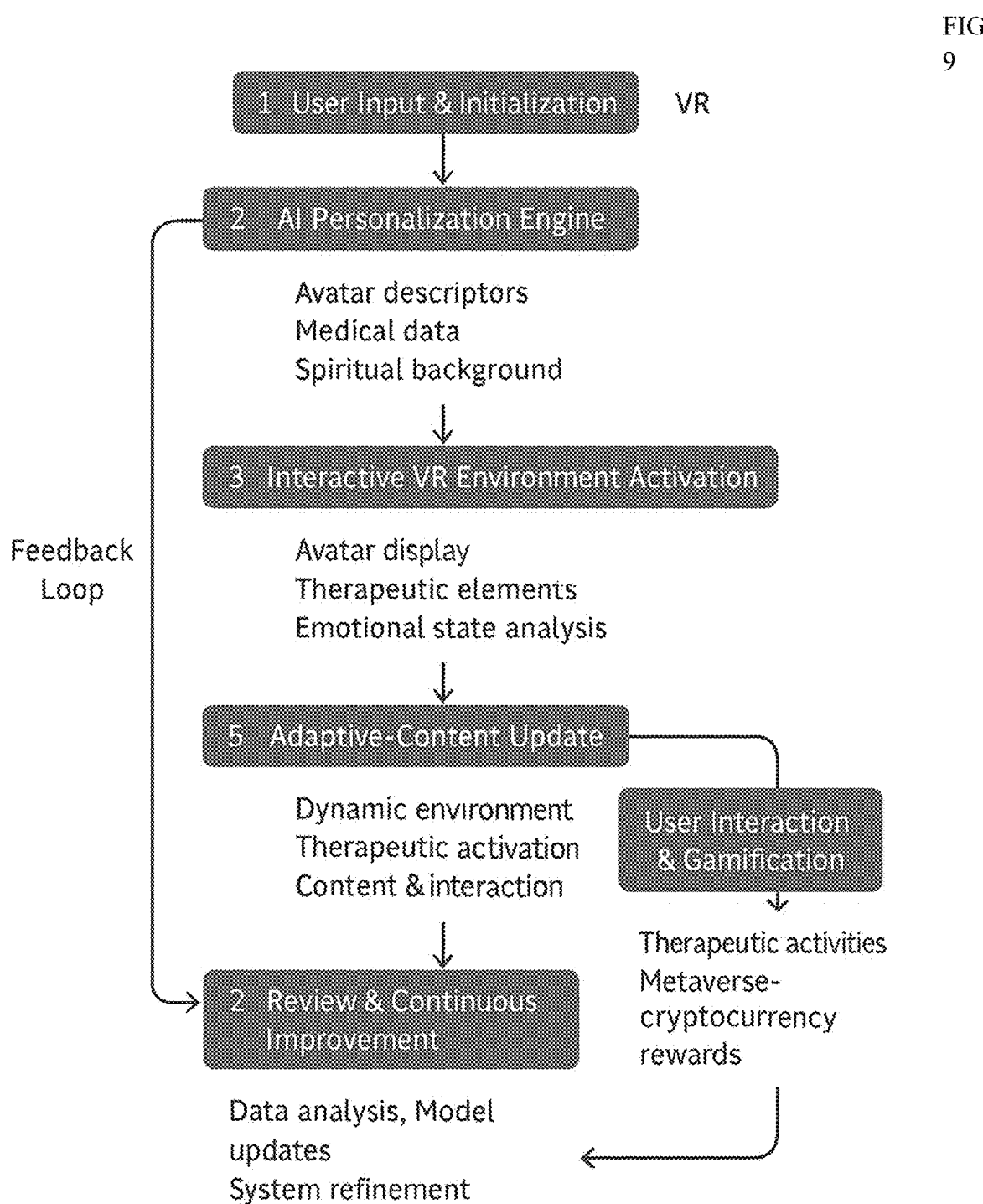
FIG. 9 illustrates a flowchart for a personalized virtual reality healthcare system.

FIG. 9 illustrates a flowchart for a personalized virtual reality healthcare system. It depicts an AI-driven therapeutic system that initiates by gathering user-specific medical, spiritual, and preference data to establish a personalized foundation. Leveraging this input, the AI generates tailored therapeutic plans, selecting audio therapies and configuring incentive mechanisms, before activating an immersive VR environment synchronized with time-marker medical data and spiritual guidance. Throughout the session, biometric metrics, emotional responses, and user interactions are tracked in real time, enabling dynamic adjustments to environmental variables, audio frequencies, and reward parameters to optimize engagement. Users participate in therapeutic exercises while earning redeemable cryptocurrency tokens, fostering sustained motivation. Concluding the process, the system aggregates session data to refine AI models, document outcomes, and enhance future personalization accuracy. The design employs a bright pastel backdrop with color-coded elements, intuitive icons, and turquoise connectors, emphasizing a closed-loop integration of healthcare, immersive technology, and blockchain-based incentives for a cohesive, adaptive user experience.

Figure 10:
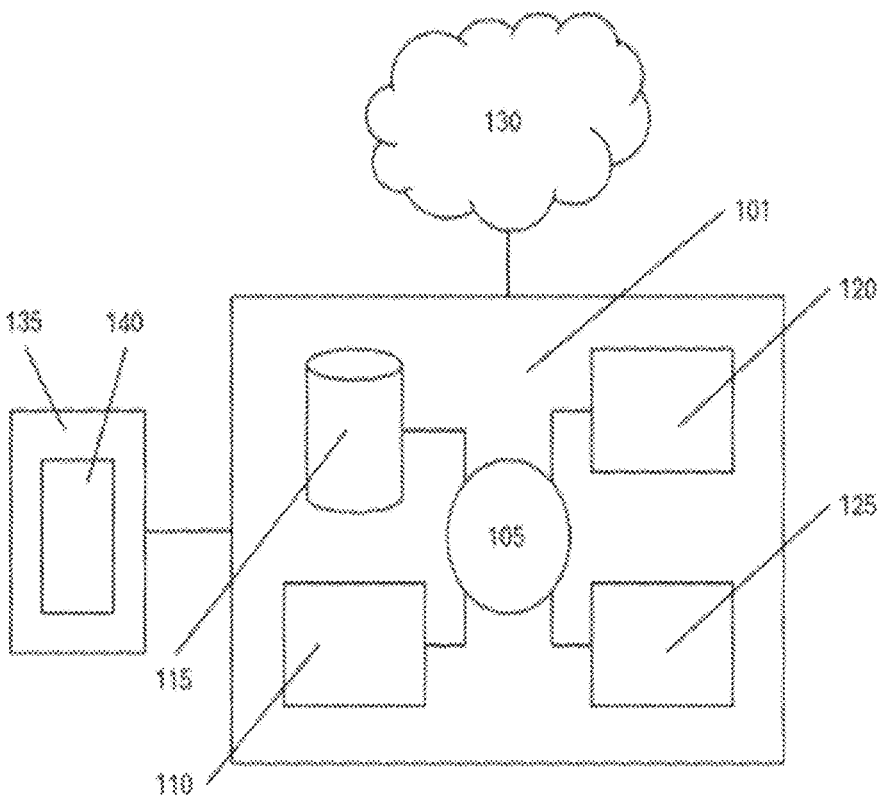
FIG. 10 illustrates a block diagram of a computer system, according to aspects of the present disclosure.

FIG. 10 illustrates a block diagram of a computer system, according to aspects of the present disclosure. The computer system 101 includes a central processing unit (CPU, also "processor" and "computer processor" herein) 105, which can be a single core or multi core processor, or a plurality of processors for parallel processing. The computer system 101 also includes memory or memory location 110 (e.g., random-access memory, read-only memory, flash memory), electronic storage unit 115 (e.g., hard disk), communication interface 120 (e.g., network adapter) for communicating with one or more other systems, and peripheral devices 125, such as cache, other memory, data storage and/or electronic display adapters. The memory 110, storage unit 115, interface 120 and peripheral devices 125 are in communication with the CPU 105 through a communication bus (solid lines), such as a motherboard. The storage unit 115 can be a data storage unit (or data repository) for storing data. The computer system 101 can be operatively coupled to a computer network ("network") 130 with the aid of the communication interface 120. The network 130 can be the Internet, an internet and/or extranet, or an intranet and/or extranet that is in communication with the Internet. The network 130 in some cases is a telecommunication and/or data network. The network 130 can include one or more computer servers, which can enable distributed computing, such as cloud computing. The network 130, in some cases with the aid of the computer system 101, can implement a peer-to-peer network, which may enable devices coupled to the computer system 101 to behave as a client or a server.

The CPU 105 can execute a sequence of machine-readable instructions, which can be embodied in a program or software. The instructions may be stored in a memory location, such as the memory 110. The instructions can be directed to the CPU 105, which can subsequently program or otherwise configure the CPU 105 to implement methods of the present disclosure. Examples of operations performed by the CPU 105 can include fetch, decode, execute, and writeback. The CPU 105 can be part of a circuit, such as an integrated circuit. One or more other components of the system 101 can be included in the circuit. In some cases, the circuit is an application specific integrated circuit (ASIC A graphics processing unit (GPU) is a specialized processing unit, electronic circuit, module, or computer chip, etc., that can accelerate digital image processing and many other applications and is often present either as a discrete video card, or embedded on motherboards, or as integrated graphics on a CPU. Similarly, chip modules are known that can perform machine learning prediction (sometimes referred to as inference). Such chips include, for example, language processing units (LPUs), cloud tensor processing units (TPUs), neural engines, AI coprocessors, AI accelerators, and neural processing units (NPUs). In some embodiments, a GPU or other chip module performs at least some of the functions that could otherwise be performed by a CPU. The storage unit 115 can store files, such as drivers, libraries and saved programs. The storage unit 115 can store user data, e.g., user preferences and user programs. The computer system 101 in some cases can include one or more additional data storage units that are external to the computer system 101, such as located on a remote server that is in communication with the computer system 101 through an intranet or the Internet. The computer system 101 can communicate with one or more remote computer systems through the network 130. For instance, the computer system 101 can communicate with a remote computer system of a user (e.g., a user, a lab technician, or a treating physician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 101 via the network 130.

Methods as described herein can be implemented by way of machine (e.g., computer processor) executable code stored on an electronic storage location of the computer system 101, such as, for example, on the memory 110 or electronic storage unit 115. The machine executable or machine-readable code can be provided in the form of software. During use, the code can be executed by the processor 105. In some cases, the code can be retrieved from the storage unit 115 and stored on the memory 110 for ready access by the processor 105. In some situations, the electronic storage unit 115 can be precluded, and machine-executable instructions are stored on memory 110. The code can be pre-compiled and configured for use with a machine having a processer adapted to execute the code or can be compiled during runtime. The code can be supplied in a programming language that can be selected to enable the code to execute in a pre-compiled or as-compiled fashion.

The computer system 101 may generate an immersive virtual reality environment for users to interact with health-related content and experiences. In some cases, the virtual reality environment may be displayed through a user interface 140. The user interface 140 may include a graphical user interface (GUI) and a web-based user interface to facilitate user interaction within the virtual environment. The user interface 140 may allow users to navigate the virtual space, interact with virtual objects, and engage with personalized health content. In some implementations, the user interface 140 may display 3D graphics rendered by the processor 105 to create a realistic and engaging virtual environment. A mobile device 135 may be integrated with the computer system 101 to provide additional functionality and data input for the virtual reality experience. In some cases, the mobile device 135 may connect to the computer system 101 through the network 130, allowing for real-time data exchange and synchronization. The mobile device 135 may serve various purposes within the virtual reality healthcare system. For example, the mobile device 135 may act as a controller for navigating the virtual environment, provide biometric data through built-in sensors, or offer an alternative display option for certain aspects of the virtual experience.

The one embodiment begins by acquiring spiritual preference data from the user. This data includes at least one spiritual archetype selected by the user, allowing for personalized customization of the virtual spiritual advisor system. This process is a foundational step in tailoring the system's functionality to align with the user's spiritual inclinations and preferences.

In one embodiment, the VMA avatar comprises a vocal modulation module configured to adjust vocal pitch and speech rate based on real-time measurements of the user's stress levels. The system gathers stress-related parameters using biometric sensors that monitor indicators such as heart rate variability, galvanic skin response, and EEG alpha/beta wave ratios. As the user's stress level increases, the module reduces the avatar's vocal pitch and speech rate; conversely, as the stress level decreases, the module raises these vocal characteristics, thereby establishing an inverse correlation between stress and the avatar's speech output. The vocal modulation module utilizes a closed-loop feedback control system that continuously acquires stress data and applies a predetermined mapping function to convert the measured stress index into corresponding pitch and rate adjustments. In certain implementations, a proportional-integral-derivative (PID) controller is employed to deliver real-time modulation, with the proportional component adjusting the vocal output in response to instantaneous stress fluctuations, the integral component accumulating stress data over time to address prolonged stress, and the derivative component anticipating rapid stress variations. The modified parameters are subsequently provided to a text-to-speech synthesis engine that dynamically alters the audio output's spectral and temporal characteristics. In some instances, smoothing algorithms are applied to the biometric data to filter out transient noise, ensuring that only significant stress changes trigger adjustments in the speech output. Furthermore, the modulation of vocal pitch and speech rate is integrated with other adaptive avatar behaviors—such as synchronized facial expressions and haptic feedback patterns—to deliver a unified response aimed at soothing the user during periods of elevated stress and promoting calm by reducing the perceived intensity of the therapeutic intervention.

The process begins with the creation of a deepfake-animated virtual avatar. This involves utilizing first-order motion models to generate realistic facial expressions and movements for the avatar, allowing it to exhibit human-like animations. This method leverages advanced animation techniques to ensure the avatar's representations are convincing and capable of maintaining user engagement.

In one embodiment, the system employs a deepfake processor generates facial muscle actuation patterns for the avatar, synchronized with phoneme output, utilizing a first-order motion model to create realistic facial expressions. The LLM generates speech in real time utilizing dynamic electronic health records and user-specific biometric data, while the deep fake technology produces smooth transitions between facial expressions. This coordinated operation enables the VMA avatar to reflect both the content and the emotional tone of the speech output, further enhancing the immersive user experience. Additionally, the system adjusts the intensity and timing of the facial animations in response to changes in the user's physiological state, as monitored by biometric sensors, ensuring the avatar's emotional expressions remain contextually relevant. The use of a first-order motion model in this configuration provides a robust framework for translating synthesized speech into realistic facial motions, which, when combined with adaptive adjustments informed by real-time data, results in a highly responsive and naturalistic animated avatar.

In one embodiment, the LLM incorporates a deep fake processing engine configured to utilize a first-order motion model to generate dynamic facial animations for the VMA avatar. The deep fake engine processes a set of reference images representing initial facial features of a trusted authority figure and, based on real-time speech synthesis outputs, computes motion vectors that correspond to salient phonetic and prosodic features of the synthesized speech. The first-order motion model encodes the motion information from the synthesized speech and applies it to the reference facial images, thereby generating a sequence of animation frames that accurately depict corresponding facial expressions synchronized with the speech output. The processing engine employs an encoder-decoder architecture where the encoder analyzes the static facial features and extracts relevant latent representations, and the decoder utilizes the motion vectors to animate the facial features in a temporally coherent manner. Furthermore, the system adjusts the intensity and timing of the facial animations in real-time based on acoustic cues, such as pitch variance and speech rate, ensuring that the avatar's expressions reflect the intended emotional tone and natural articulation of the synthesized speech. The method also includes post-processing steps to refine the synchronization between lip movements and phoneme output, thereby enhancing the authenticity of the deep fake animation.

In certain embodiments, the VMA avatar is configured to cross-reference one or more medication databases to visually indicate potential drug interactions within a virtual pharmacy interface. The system gathers medication-related information from databases containing data on drug properties, known interaction pairs, contraindications, and dosage recommendations. The VMA avatar uses natural language processing and pattern matching algorithms to compare a user's current medication regimen with this database information to identify potential interactions. When a drug interaction is detected, the system dynamically generates visual alerts that overlay on the virtual pharmacy interface. These alerts incorporate color-coded icons, highlighted text, or graphical indicators that denote varying levels of interaction severity. In addition, the avatar presents supplementary contextual information regarding the interaction, including a brief description, recommended warnings, or suggested changes in the medication regimen. This process integrates into the interactive experience such that as the user navigates the virtual pharmacy interface, the VMA avatar continuously updates the display in real time based on current user medication data and the most recent database information. The system also incorporates predictive analytics to forecast potential interactions based on historical user data, thereby enhancing user safety and supporting informed decision-making for medication management.

In one embodiment, the deepfake animation utilizes facial landmark detection with a 68-point facial mesh warping technique. The system processes an input facial image by first detecting a set of 68 facial landmarks corresponding to predetermined anatomical features including, but not limited to, the corners of the eyes, the contours of the eyebrows, the tip of the nose, the outline of the lips, and the jawline. The detected landmarks are then used to generate a facial mesh that defines a network of interconnected triangles overlaying the subject's face. The points of the mesh align precisely with the detected landmarks, enabling the system to capture fine-grained facial expressions and subtle movements. A warping algorithm is then applied to the mesh, deforming the facial image according to motion parameters derived from either real-time input or pre-recorded reference data. In some implementations, the deformation process involves calculating affine transformations for each triangular segment of the mesh, ensuring that transitions between frames remain seamless and continuously account for variations in facial expressions. The resultant deepfake animation accurately reflects the dynamic range of the subject's expressions by mapping the motion of the detected landmarks onto corresponding areas of a target face model, further refining lip synchronization with phoneme outputs by dynamically adjusting the mesh in accordance with speech-related movements. The system also employs additional techniques such as temporal smoothing filters and facial action unit analysis to improve the warping process and mitigate potential artifacts. By incorporating a 68-point facial mesh, the deepfake animation achieves a degree of realism and precise control over individual facial features, thereby improving the overall fidelity of avatar representation in immersive environments.

In some embodiments, the system further comprises implementing a two-phase reinforcement learning process wherein, in a pre-training phase, historical interaction data is employed to initialize and optimize the behavioral models governing avatar actions and content delivery strategies; the historical data, comprising prior user interactions and system responses, is processed using established techniques to establish baseline policy parameters. Subsequently, during a fine-tuning phase, proximal policy optimization (PPO) is applied in conjunction with feedback obtained from human advisors to refine these policy parameters in real time. The PPO process adjusts the avatar's decision-making framework by comparing predicted outcomes against human advisor feedback and actual user engagement metrics, thereby ensuring that therapeutic guidance is continuously adapted to align with clinically validated protocols and user-specific responses. This two-phase reinforcement learning approach, by integrating pre-training on historical data with fine-tuning guided by expert human input, improves the dynamic adjustment of avatar behaviors, ultimately enhancing the responsiveness and efficacy of the personalized therapeutic interventions delivered within the immersive virtual environment.

Biometric Monitoring and Real-Time Adjustments

The process involves analyzing electroencephalography (EEG) signals to identify when the alpha to beta brain wave ratio drops below a value of 0.8. This analysis allows for real-time monitoring of the user's mental state, enabling the system to adjust the virtual spiritual advisor avatar's responses accordingly.

In one implementation, the virtual spiritual advisor (VSA) avatar's vocal parameters are modified according to heart rate variability (HRV) metrics. This involves adjusting the avatar's vocal tone and speech to reflect the user's physiological state, as determined by fluctuations in HRV. Through this process, the avatar can provide more personalized and responsive interaction, enhancing the user's immersive experience.

The process described involves handling EEG signals by employing Butterworth filters. This filtering helps detect alpha/beta wave ratios below 0.8, achieved through a biosignal processing pipeline. This action allows for a detailed analysis of specific brain wave patterns essential for the operation of the virtual spiritual advisor system.

In one embodiment, the biometric sensors include an EEG headset configured to detect brain electrical activity and, more specifically, to measure alpha and beta wave ratios as an indicator of anxiety states. The EEG headset captures neural signals that are processed by a biosignal processing module, which extracts frequency components corresponding to the alpha and beta bands. The system computes a ratio of the alpha to beta wave amplitudes and compares this ratio to predetermined threshold values to determine whether the detected neural activity is indicative of an anxiety state. When a reduced alpha/beta ratio is observed, which has been correlated with heightened anxiety, the system initiates adaptive therapeutic responses by dynamically adjusting the virtual avatar's emotional tone, speech patterns, and the content of therapeutic interventions. The headset incorporates noise-reduction features, such as bandpass filtering using a Butterworth filter, to ensure the fidelity of the captured EEG signals and to minimize the impact of extraneous electrical interference. Furthermore, calibration routines are employed to account for individual baseline differences in neural activity, thereby enhancing the accuracy of anxiety detection. This measurement approach enables the system to provide real-time adjustments to the therapeutic interaction, thereby improving the overall efficacy of the intervention.

In various embodiments, the system continually monitors the user's electroencephalogram (EEG) signals for alpha wave dominance using a biometric integration module. When the measured alpha wave dominance falls below a predetermined threshold, the artificial intelligence (AI) controller activates a preprogrammed routine within the virtual medical avatar (VMA). The VMA initiates a series of guided breathing exercises designed to promote relaxation and restore a desirable physiological state. In these embodiments, the VMA presents synchronized visual and auditory cues to guide the user through structured inhalation, holding, and exhalation sequences. The visual cues include pulsating or expanding images corresponding to the breathing cycle, while the auditory cues incorporate calming tone modulations that align with the breathing rhythm. In certain cases, haptic feedback provided through wearable devices is employed to reinforce these cues by delivering gentle tactile pulses in synchrony with the breathing instructions. A predetermined threshold for alpha wave dominance is established during an initial calibration phase, which allows the system to tailor intervention intensity based on individual baseline measurements. Additionally, the system adjusts the duration, frequency, and pacing of the breathing exercises in real-time, taking into account both the degree of deviation from the threshold and the historical responsiveness of the user to previous interventions. This dynamic adjustment enables the avatar to deliver personalized and adaptive therapeutic content that addresses acute fluctuations in the user's physiological state. The integration of real-time EEG monitoring with responsive avatar behavior forms a closed-loop system for optimizing user relaxation and enhancing overall treatment efficacy.

The system further comprises a real-time rendering engine that integrates a Monte Carlo simulation module configured to generate a plurality of probabilistic health trajectories based on user compliance metrics. In particular, the Monte Carlo simulation module performs iterative simulation runs that model potential health outcomes by incorporating stochastic variations associated with patient adherence data, such as medication intake timing, exercise routines, dietary patterns, and attendance in therapeutic sessions. The outcome of these simulation runs is a series of dynamic visualizations that are overlaid onto three-dimensional anatomical models or other graphical representations of health status, thereby enabling the depiction of various potential outcome pathways. The visualizations represent the probabilistic distribution of future health states, reflecting the degree of compliance to prescribed therapeutic regimens. Furthermore, the Monte Carlo simulation module continuously updates the probabilistic health trajectories in response to real-time adjustments in compliance metrics captured by the biometric and sensor systems, ensuring that the displayed outcomes accurately mirror current engagement levels. This integration facilitates an intuitive understanding of the relationship between patient behavior and predicted health outcomes, and it allows both clinicians and patients to assess the potential impact of enhanced adherence on sustained health trajectories.

In some embodiments, the system dynamically adjusts Solfeggio frequency amplitudes inversely proportional to detected stress biomarkers. In these embodiments, real-time biometric data, including galvanic skin response and heart rate variability, is continuously monitored and processed using a biosignal processing pipeline to generate a stress index. This stress index, representing current physiological stress levels, is used to modulate the amplitude of therapeutic audio signals such that an increase in the detected stress biomarker level results in a proportionate decrease in the Solfeggio frequency amplitude, and conversely, a decrease in the stress index leads to an increase in the audio amplitude. The system employs control algorithms, such as proportional-integral-derivative controllers, to effectuate these adjustments, thereby ensuring that the amplitude of the audio output is maintained at an optimal level relative to the user's stress state. During an initialization phase, baseline stress parameters are established and subsequently used to calibrate the adaptive feedback mechanism. As the user's biometric data is acquired in real time, the system computes an updated stress index and applies an inverse scaling factor to adjust the Solfeggio frequency amplitudes accordingly. For instance, an increase in the stress index by a defined magnitude will trigger a predetermined corresponding reduction in the frequency amplitude, while a decrease in the stress index will result in an incremental increase of the amplitude. This adaptive modification technique enables the therapeutic audio output to dynamically respond to changing physiological conditions, thereby optimizing the efficacy of the audio meditation intervention and ensuring that the auditory environment is continuously tailored to enhance user relaxation and well-being.

These dynamic adjustments are implemented using a feedback control algorithm that compares real-time sensor data with baseline calibrated values. When deviations from expected values are detected, the algorithm triggers alterations in the audio signal parameters to maintain optimal therapeutic engagement while promoting relaxation or alertness according to the treatment protocol. The method further incorporates predefined thresholds and adaptive learning elements that progressively refine the modulation parameters over multiple therapy sessions to enhance treatment efficacy and personalization over time.

In one embodiment, the system further comprises wearable devices configured to provide haptic feedback patterns that are phase-locked to brainwave synchronization events in the theta (4-8 Hz) and gamma (30-100 Hz) frequency bands. In this embodiment, EEG sensors integrated into the system continuously monitor neural activity and generate signals indicative of brainwave synchronization events. A processing module analyzes these signals in real time to detect characteristic oscillatory patterns corresponding to theta and gamma frequencies. Upon detection, a control module coordinates the triggering of haptic feedback patterns delivered by the wearable devices. These haptic patterns synchronize with the phase of the detected brainwave events, ensuring that the timing of the feedback is tightly coupled to the subject's neural activity. Furthermore, the control module dynamically adjusts feedback parameters such as intensity, duration, and frequency composition based on the amplitude and consistency of the detected neural signals. The phase-locked haptic feedback is configured to enhance sensory stimulation in a closed-loop manner, thereby supporting cognitive engagement and therapeutic outcomes. This integration of real-time EEG monitoring with phase-locked haptic feedback provides an additional layer of interactivity, aligning tactile stimulation with endogenous brain rhythms to facilitate a more immersive and responsive therapeutic experience.

In one embodiment, the augmented reality environment is configured to render real-time audiographic representations of autonomic nervous system balance by leveraging particle systems that are dynamically responsive to heart rate variability metrics. The system receives biometric data from wearable sensors, which is processed to derive heart rate variability values indicative of sympathetic and parasympathetic modulation. An analysis module maps these HRV metrics to corresponding particle system parameters, wherein alterations in HRV prompt adjustments in particle generation rate, motion vectors, color intensity, and spatial distribution within the AR display. Concurrently, an audio rendering engine converts these dynamic particle parameters into complementary auditory cues, modulating pitch, volume, and rhythm in direct correlation with the real-time HRV data. The resulting audiovisual output provides an integrated representation wherein the particle system visually and sonically manifests the balance of autonomic nervous system activity, enabling users to perceive fluctuations in real time. A closed-loop feedback mechanism is employed wherein continuous HRV monitoring allows the system to adjust both the graphical particle attributes and the associated audio signals, thereby ensuring that the audiovisual representation remains synchronized with the underlying physiological state. Such an arrangement facilitates an immersive user experience that aids in self-monitoring and potentially in guiding therapeutic interventions based on autonomic nervous system balance.

In embodiments of one implementation, the system further comprises training a bidirectional encoder representations from transformers (BERT) model on tokenized sacred texts using byte-pair encoding with 512-token context windows. The training process involves segmenting sacred texts stored in non-transitory memory into token sequences wherein byte-pair encoding is applied to efficiently represent recurring subword patterns. The resulting tokenized sequences are organized into context windows of 512 tokens each, which serve as the input to the BERT model. The model is then trained to learn contextual representations and semantic relationships inherent to the sacred texts, thereby enabling the extraction of spiritually relevant concepts and facilitating semantic similarity matching with user-declared beliefs. This training process is integrated into the broader framework of adaptive therapeutic content generation, wherein the output of the BERT model is utilized in the generation of personalized spiritual guidance by the virtual spiritual advisor (VSA) avatar. The BERT model, trained on the sacred texts, contributes to the generation of therapeutic content that is reflective of the user's spiritual preferences by enabling precise retrieval and synthesis of relevant excerpts from sacred text databases. This approach enhances the overall personalization and efficacy of the therapeutic interventions provided through the avatar-based system by ensuring that the delivered spiritual content is both contextually and semantically aligned with the user's declared spiritual archetype.

In one embodiment, the haptic feedback subsystem receives real-time galvanic skin response signals from integrated sensors, and the system adaptively calibrates thresholds based on baseline measurements obtained during periods of minimal stress. The real-time GSR data is processed through a control unit that continuously monitors variations in the intensity of the electrodermal response and applies statistical algorithms to determine dynamic thresholds tailored to the individual user's physiological profile. When the real-time GSR measurement exceeds the adaptive threshold, the control unit triggers the haptic feedback subsystem to deliver a vibrotactile stimulus, with the feedback pattern synchronized to the user's cardiac rhythm and other biometric parameters. This adaptive threshold triggering mechanism involves periodically recalculating the threshold values by comparing accumulated historical GSR data with current measurements, thereby ensuring that the feedback intensity remains within a therapeutically relevant range. As a result, the haptic feedback patterns are effectively correlated with fluctuations in the user's galvanic skin response, enabling responsive, personalized modulation of tactile stimuli that enhance the overall therapeutic experience.

In some embodiments, the system further comprises one or more photoplethysmography (PPG) sensors operable to detect microvascular changes during VMA-guided exposure therapy sessions. The PPG sensors acquire reflected electromagnetic energy from the user's skin and convert the resulting signal into digital data indicative of pulsatile blood volume variations, which correlate to microvascular activity within the user's tissue. The digital output is then processed by a biometric integration module that employs noise reduction and signal filtering techniques to eliminate artifacts and motion-induced disturbances, thereby yielding a reliable measurement of microvascular changes. The processed data are analyzed to determine variations in cardiovascular parameters relevant to stress and relaxation responses, such as pulse transit time and derived cardiovascular stress indices. These measurements are subsequently integrated with other biometric signals, such as heart rate variability and galvanic skin response, to provide a comprehensive assessment of the user's physiological state. This integrated physiological profile is employed by an AI controller to dynamically adjust the VMA's therapeutic output by modulating verbal content, emotional tone, and interactive cues in real-time. In this manner, the microvascular data obtained via the PPG sensors contributes to a feedback loop that refines the exposure therapy session, thereby enhancing the precision and personalization of the therapeutic intervention administered by the VMA.

Therapeutic Audio and Haptic Feedback

In one embodiment, the system further comprises generating therapeutic audio frequencies that include Solfeggio frequencies between 174 Hz and 963 Hz, wherein these frequencies are synchronized with the VMA avatar's speech output. In this configuration, a digital signal processing module is configured to generate and modulate the therapeutic audio frequencies concurrently with the avatar's synthesized speech to achieve precise temporal alignment between the spoken words and the accompanying auditory cues. The generated audio frequencies are dynamically adjusted based on real-time biometric feedback, ensuring that the therapeutic content delivered by the VMA avatar is enhanced by synchronized auditory stimulation. This synchronization is accomplished by correlating the avatar's speech prosody and phoneme patterns with the timing and amplitude modulation of the Solfeggio frequency signals. In certain embodiments, the therapeutic audio frequencies are rendered through audio output devices such as bone conduction transducers or standard speakers, thereby providing an integrated multisensory experience in immersive VR or AR environments. The system's ability to continuously monitor physiological data facilitates real-time adaptation of both the avatar's speech parameters and the corresponding audio frequencies, further optimizing the therapeutic efficacy of the session.

In one embodiment, the system further comprises triggering haptic feedback through one or more wearable devices synchronized with the VMA avatar's procedural demonstrations. In this embodiment, the controller coordinates the timing of the haptic feedback with specific moments in the avatar's demonstration sequence to enhance the user's immersion and comprehension of the presented procedures. The wearable devices, which include a vest, wristbands, or other body-worn apparatuses, are configured to receive control signals from the AI controller. The controller dynamically modulates the feedback signals based on the real-time physiological data gathered from biometric sensors and the progression of the avatar's procedural demonstrations. The haptic feedback is generated by activating actuators in the wearable devices in patterns that synchronize with the rhythm and emphasis of the VMA avatar's demonstration steps. For example, as the avatar highlights a particular instruction or performs an essential maneuver, the system outputs a corresponding vibration or pulse through the wearable device to provide tactile reinforcement to the user. This integration of haptic feedback with the avatar's procedural demonstrations not only complements the visual and auditory outputs but also reinforces the overall experiential learning by engaging the user's sense of touch. The synchronization is achieved by processing temporal cues from the avatar's demonstration progress and applying them to modulate the intensity, frequency, and duration of the haptic signals in the wearable devices. Moreover, the system can adjust the haptic feedback parameters in real time based on changes in the user's physiological state, thereby assuring that the intensity of the tactile stimulation is appropriate to the user's current engagement and stress levels. This further comprising feature enhances user interaction by providing a multi-sensory approach to procedural learning that integrates visual, auditory, and tactile modalities into a unified therapeutic session.

In certain embodiments, the system incorporates an audio processing module configured to dynamically modulate isochronic tones in a way that maintains a constant 1:2 phase relationship with the dominant respiratory sinus arrhythmia rhythms detected from the user. The system first acquires real-time physiological data using appropriate sensors—including those measuring heart rate variability and respiratory patterns—from which the dominant respiratory sinus arrhythmia rhythm is derived. A phase detection unit within the audio processing module analyzes the incoming respiratory signals to determine the timing of the dominant rhythm cycle and establishes a reference phase for modulation. Based on this analysis, a tone modulation submodule adjusts the temporal parameters of the isochronic tones such that for each cycle of the respiratory rhythm, two corresponding auditory pulses are generated with a fixed phase offset relative to the breathing cycle. The modulation submodule continuously monitors the respiratory sinus arrhythmia signals and recalculates the phase offset as necessary to maintain the predetermined 1:2 phase relationship despite any fluctuations in the breathing pattern. Digital signal processing techniques, including fast Fourier transforms and phase correlation analyses, are employed to accurately identify the dominant respiratory frequency and determine the optimal timing for tone pulses. In some embodiments, adaptive filtering is used to minimize noise and ensure that the detected respiratory rhythm is reliably isolated from extraneous signals, thereby allowing precise control of the phase modulation. The dynamically modulated isochronic tones, after adjustments in frequency, amplitude, and timing, are delivered through audio transducers integrated into the system, such as bone conduction transducers. The resulting synchronized auditory environment is intended to enhance user relaxation and promote physiological entrainment in therapeutic sessions.

In one embodiment, the system further integrates therapeutic audio components with augmented reality (AR)-guided mindfulness exercises. The system generates spatialized voice prompts that are adaptively modulated in cadence based on real-time estimates of cortisol levels. In this embodiment, the system continuously monitors the user's biochemical state using sensors configured to derive cortisol level estimates, which are then transmitted to a processing module. The processing module computes the current cortisol level and provides control signals to dynamically adjust the cadence of voice prompts. The adjustment is governed by an inverse proportionality function such that reduced cortisol levels result in a relatively higher cadence of voice prompts while elevated cortisol levels yield a decelerated cadence. This inverse relationship is mathematically modeled as a function in which the cadence factor is proportional to a calibration constant divided by the instantaneous cortisol level, thereby ensuring that therapeutic audio pacing is modulated in real time to reflect the user's stress state. The spatialized voice prompts are rendered via bone conduction transducers integrated into an AR headset, enabling the audio cues to be perceived as emanating from specific spatial locations within the user's AR environment. In addition to the cadence modulation based on cortisol estimates, the system synchronizes the auditory guidance with visual AR cues that direct the user through mindfulness exercises such as guided breathing techniques and focused visualizations. The system further refines the cadence adjustment by incorporating additional biometric feedback, including heart rate variability and galvanic skin response, which are processed through a temporal convolutional network to calibrate the inverse proportionality function in a dynamic and adaptive manner. This holistic integration of real-time biochemical and physiological data with AR-guided, spatialized therapeutic audio serves to optimize the mindfulness exercise by ensuring that the delivery of voice prompts remains adaptive to the user's immediate stress levels, thereby potentially enhancing the overall efficacy of the therapeutic intervention.

The system further incorporates an additional module configured to cross-reference a pharmaceutical database in real time to audibly highlight potential interactions between current medications and specific therapeutic frequency ranges. In embodiments, after extracting the user's medication data from electronic health records, the system queries an integrated pharmaceutical database to retrieve documented medication profiles and known interactions related to designated audio frequencies, including those corresponding to therapeutic signals. Upon identifying a correlation between the user's current medication regimen and defined frequency ranges that could pose interaction risks, the system generates audible alerts. These alerts are synthesized as part of the personalized virtual medical avatar's speech output, with the vocal delivery dynamically modulated in pitch, tone, and rhythm to emphasize potential concerns. In specific embodiments, the audible alert is delivered within an immersive VR or AR environment and seamlessly integrated into ongoing therapeutic sessions, ensuring that the user is promptly informed of any potential pharmacological-auditory interactions. This process operates concurrently with continuous biometric monitoring, enabling the system to adjust therapeutic audio parameters while maintaining user safety. The integration of the pharmaceutical database cross-referencing module thereby enhances patient safety by providing immediate, adaptive content modulation that prompts the user to seek further medical guidance or adjust therapeutic regimens accordingly.

In one exemplary embodiment, the AR glasses are configured to implement beamforming techniques designed to isolate therapeutic audio signals from environmental noise levels exceeding 65 dB SPL. In this embodiment, an array of directional microphones and speakers integrated within the AR glasses cooperatively function to detect, localize, and suppress extraneous noise while simultaneously enhancing the clarity and fidelity of the intended therapeutic audio output. The system continually samples ambient noise levels and dynamically adjusts the beamforming parameters to target sound sources selectively, ensuring that the delivered therapeutic audio remains discernible even when ambient sound exceeds the specified threshold. Furthermore, the method includes utilizing a generative adversarial network (GAN) to synthesize personalized binaural compositions that are tailored based on individual music preference profiles and corresponding stress biomarker patterns. In this configuration, the GAN is trained on a dataset that comprises user-specific musical tastes as well as physiological data collected during stress events. The network generates binaural audio compositions that are optimized both in terms of acoustic properties and in their ability to induce a targeted therapeutic effect, such as relaxation or stress mitigation. The integration of the GAN ensures that the personalized audio output continuously evolves in response to real-time biometric feedback, thereby enhancing the overall efficacy of the therapeutic intervention in dynamic environments.

In one embodiment, the system modulates interaural level differences to create virtual sound source movements that are synchronized with guided visual focus exercises. The system adjusts the amplitude of audio signals delivered to each ear in real-time, thereby creating a perception of a moving sound source that directs the user's attention in accordance with pre-programmed visual focal points. The modulation of these audio signals is coordinated with corresponding visual cues generated by the system, ensuring that the movement of the virtual sound source aligns seamlessly with the guided visual focus exercises.

In further embodiments, the method implements differential privacy filters on raw electroencephalography data to enhance privacy during federated learning updates to the audio personalization models. In these embodiments, raw EEG data is first processed through a differential privacy framework which adds a controlled level of random noise, or applies other anonymization techniques, to prevent the extraction of individually identifying information. This privacy-preserving processed data is then used during the federated learning update process to train and refine audio personalization models across multiple nodes or devices without compromising the privacy of the original data. The combination of interaural level difference modulation synchronized with visual stimuli and the incorporation of differential privacy in the federated learning process ensures that personalized audio cues are provided in a manner that is both immersive for the user and compliant with privacy standards.

In one embodiment, the therapeutic audio signals are generated to incorporate stochastic resonance patterns that are calibrated to enhance signal detection in auditory processing pathways. In this arrangement, a digital signal processor is configured to introduce a controlled level of noise into the audio output such that the noise interacts with weak sensory inputs, thereby improving the signal-to-noise ratio within central auditory processing circuits. The stochastic resonance protocol is dynamically modulated in real time based on biometric feedback, ensuring that the amplitude and frequency characteristics of the noise are maintained at levels optimized for enhanced neural processing.

In one embodiment, the system generates therapeutic audio frequencies that include isochronic tones modulated at 10 Hz delta wave patterns. The isochronic tones are digitally produced and modulated by a dedicated audio processing module, wherein a carrier audio signal is pulsed at a modulation frequency of approximately 10 Hz to generate periodic intensity variations corresponding to delta brainwave frequencies. The digital audio processor employs algorithms based on Fourier synthesis and time-domain modulation techniques to ensure precise pulse timing and amplitude control. The resulting audio signal is rendered through bone conduction transducers or integrated speakers within the virtual reality headset, enabling spatially localized audio delivery within the immersive environment.

Real-time biometric sensor feedback, including electroencephalogram (EEG) and heart rate variability data, is utilized to continually assess the user's neurophysiological state, with modulation parameters dynamically adjusted to maintain optimal synchronization with the user's endogenous delta rhythms. A reinforcement learning module receives biometric data and evaluates user response, adapting the amplitude, duty cycle, and temporal characteristics of the isochronic tones to achieve better therapeutic outcomes. Additionally, the controller monitors the spectral content of the output signal using real-time digital signal processing to verify that the modulation remains within the specified 10 Hz range, making micro-adjustments if any deviations are detected.

In certain embodiments, the system further comprises optimizing avatar gaze patterns using inverse reinforcement learning derived from recorded clinician-patient interactions. In these embodiments, recorded sessions capturing clinician head movements, eye gaze trajectories, and related contextual communication cues are analyzed by an inverse reinforcement learning module. This module infers gaze control policies that closely emulate natural clinician behavior. The system then integrates these policies into the avatar control framework so that the avatar dynamically adjusts its gaze direction during interactions. By aligning the avatar's nonverbal communication signals with those observed in clinician-patient interactions, the system enhances the naturalness and therapeutic effectiveness of the interaction. This optimization is carried out concurrently with adjustments to speech patterns, emotional tone, and other therapeutic content, ensuring that the gaze behavior reinforces the overall clinical intent. Moreover, the system periodically updates the inferred policies based on new interaction data, thereby continuously refining the avatar's gaze patterns to maintain a robust level of realism and connection during therapeutic sessions.

NLP, Data Processing, and Machine Learning

The system employs a natural language processing (NLP) module that analyzes unstructured clinical notes from electronic health records (EHRs) using a bidirectional encoder representations from transformers (BERT) architecture. In one embodiment, the NLP module converts the unstructured text into a sequence of tokens and embeds these tokens into continuous vector representations that capture both syntactic and semantic information. The BERT-based model processes this embedded data by considering the bidirectional context of the text, enabling the system to accurately identify relevant clinical features such as diagnoses, medications, symptoms, and treatment plans. The model utilizes masked language modeling and next sentence prediction methods during training, which enhances its ability to derive contextual relationships among words and phrases within the clinical notes. This contextual understanding allows the NLP module to extract pertinent health information necessary for tailoring the medical advice provided by the virtual medical authority (VMA) avatar. Furthermore, the BERT architecture is fine-tuned using a comprehensive dataset comprising medical literature and clinical data to improve its accuracy and reliability in the healthcare domain. As a result, the system is capable of delivering personalized medical information that is dynamically updated based on the latest extracted data, ensuring that the therapeutic content communicated by the VMA avatar aligns with the specific clinical context of the user's health condition.

In one embodiment, the system receives unstructured clinical notes from electronic health records and processes them using a bidirectional encoder representations from transformers (BERT) architecture. The unstructured text is first tokenized and normalized to ensure consistency across diverse input formats. The BERT model then applies a multi-layer attention mechanism to capture contextual relationships between clinical terms and phrases, thereby identifying salient semantic features such as symptoms, diagnoses, treatments, and patient history. The output from the BERT model is subsequently mapped to structured clinical concepts using standardized medical ontologies, such as those provided by the Unified Medical Language System, to facilitate further processing by other system components. The extracted clinical information is integrated into the avatar's behavior by informing the selection and sequencing of medically relevant content, ensuring that the therapeutic guidance delivered is tailored to the patient's current health conditions. In certain embodiments, the BERT-based analysis includes confidence scoring and thresholding to validate the extracted clinical concepts prior to their use in dynamic content generation. Furthermore, the system is configured to learn from ongoing interactions, allowing the BERT architecture to be periodically retrained using additional clinical notes and feedback, thereby refining the precision of its analysis over time. This process ultimately enables the system to adapt its therapeutic recommendations in real time based on the most current and contextually relevant clinical data.

In one embodiment, the method further comprises generating spiritual content wherein a semantic similarity matching module compares extracted concepts representing user spiritual goals with annotations associated with a plurality of scriptural passages. In this context, the semantic similarity matching employs cosine similarity calculations between user spiritual goals and annotated scriptural passages. The cosine similarity is calculated by representing both the user spiritual goals and the scriptural passages in a common vector space, wherein each vector component corresponds to a pre-defined semantic feature derived from the scriptural content and user input. The process involves normalizing the feature vectors to unit length and then computing the cosine similarity as the dot product of the two vectors. When the computed cosine similarity exceeds a predetermined threshold, the system selects the scriptural passages with the highest similarity scores to provide spiritual guidance tailored to the user's expressed spiritual preferences. The selected scriptural passages are then integrated with the avatar-delivered content, thereby delivering bespoke spiritual input during therapeutic sessions. This process allows for the dynamic adaptation of spiritual content in response to user interactions and ensures that the content remains relevant and personalized throughout the session.

In embodiments involving transformer-based architectures (e.g., BERT) or other deep learning models that derive clinical concepts and assess medication adherence patterns, the XAI module leverages corresponding internal weightings to assign importance levels to individual clinical features and biometric parameters. The module is also configured to cross-reference feature importance weights with outputs from reinforcement learning modules that optimize avatar emotional tone and content delivery. Furthermore, in certain embodiments, the XAI module records snapshots of the generated visualizations, including the respective feature importance weights, in a secure blockchain ledger, thus providing an auditable history of decision-making processes and enhancing transparency. The integration of the XAI module thereby facilitates enhanced interpretability of the system's medical recommendations while bolstering user trust and enabling clinicians and users to validate how specific input parameters influence the overall therapeutic outcome.

VMA

The CINT system incorporates a Personalized Virtual Medical Advisor (VMA), designed to enhance patient education and engagement by providing tailored medical information in an interactive and supportive manner. This system offers several key functions that promote patient understanding and participation in their healthcare. Personalized Education is a core feature of the VMA, delivering customized educational content that explains the patient's specific medical condition, the mechanisms of action for prescribed medications, and their individualized treatment plan. This approach empowers patients to take an active role in their healthcare by fostering a deeper understanding of their condition and treatment options. Additionally, the VMA encourages Active Learning through interactive elements such as quizzes, questions, or simulations that reinforce learning and assess comprehension.

The VMA also provides Emotional Support by utilizing sentiment analysis to detect and respond to the patient's emotional state in real-time. It offers reassurance, support, and encouragement, particularly when patients express negative emotions like anxiety or fear. The VMA tailors its communication style and content to meet the patient's emotional needs, creating a safe and supportive learning environment. In real-world scenarios, the VMA can be utilized in various clinical settings. For instance, a patient newly diagnosed with breast cancer could use the VMA to receive a personalized explanation of their specific type and stage of cancer, understand treatment options, and learn about chemotherapy side effects. Similarly, patients prescribed new medications for conditions like hypertension can interact with the VMA to learn about the medication's mechanism of action, potential side effects, and proper administration. The VMA can also support patients undergoing physical therapy after a stroke by providing personalized exercise instructions, tracking progress, and offering encouragement. Additionally, it helps manage chronic conditions like diabetes by educating patients on blood sugar management, diet, exercise, and medication adherence.

To foster trust and engagement, the VMA allows patients to select an avatar they feel comfortable with. This includes familiar figures like healthcare professionals, culturally relevant avatars, or even customizable avatars created using a character creation tool. This personalized avatar selection helps establish a rapport between the patient and the VMA, enhancing the learning environment.

The VMA delivers educational content through Tailored Video Content, explaining complex medical information in an accessible manner. These videos cover topics such as specific medical conditions, medication mechanisms of action, and individualized treatment plans. The content is personalized by referencing the patient's medical records and incorporating the latest medical guidelines and research.

The VMA leverages Advanced AI Technologies to deliver a personalized and interactive experience. It uses deepfake generation to create realistic avatars with lifelike expressions and voice cloning, enhancing the VMA's presence and relatability. Natural Language Processing (NLP) enables the VMA to accurately answer patient queries, while sentiment analysis detects and responds to the patient's emotional state, providing appropriate support and reassurance. This comprehensive approach represents a significant advancement in healthcare systems, combining AI technologies to create a uniquely adaptive and responsive therapeutic environment that can improve patient outcomes and treatment adherence.

VSA

The Personalized Virtual Spiritual Advisor (VSA) within the CINT system plays a pivotal role in providing tailored spiritual support and guidance. It serves several key functions, including offering personalized spiritual guidance that is customized based on individual beliefs, preferences, and needs. This guidance adapts to different spiritual backgrounds and provides resources relevant to specific goals, such as stress reduction or finding meaning. The level of guidance is also adjusted according to the user's comfort level with spiritual practices.

The VSA offers a variety of tailored spiritual practices, including guided or interactive prayer sessions, meditation techniques like mindfulness or loving-kindness, and contemplative exercises. These practices are carefully aligned with the patient's specific spiritual background and preferences, ensuring a meaningful and relevant experience. Additionally, the VSA integrates relevant passages from sacred texts such as the Bible, Bhagavad Gita, and Buddhist Sutras. This integration provides comfort, inspiration, and guidance specifically aligned with the patient's condition, goals, and spiritual tradition.

The VSA promotes a holistic healing approach by combining spiritual guidance with medical treatment. This integrated approach recognizes the interconnectedness of mind, body, and spirit, acknowledging that spiritual well-being can positively influence mental and physical health outcomes. Patients can select their spiritual guide from diverse options, including standard system avatars, well-known figures (with permissions), or customizable avatars. This customization enhances the effectiveness of the VSA by aligning it with user values, fostering credibility and trust, and creating a safe space for exploration and self-discovery.

The AI-driven system matches users with appropriate VSA profiles and adapts the experience dynamically. It analyzes user responses, spiritual beliefs, values, and preferences to identify potential VSA archetypes using rule-based systems and machine learning models. The system adjusts the VSA's communication style and content based on user feedback and engagement, ensuring a personalized journey that is both meaningful and motivating.

In integrating sacred texts, the VSA uses AI algorithms to select passages based on the patient's spiritual background and current needs. It provides context and interpretation for these passages, ensuring they are understood and applied in a meaningful way. This personalized delivery enhances spiritual support and fosters a deeper connection with the patient's faith. Ethical considerations are paramount in the CINT system. Transparency is maintained by clearly disclosing the AI-generated nature of the VSA and providing disclaimers to distinguish it from actual public figures. Patients are informed about the use of authority figures and given the choice to opt out or select alternative avatars. The system ensures accuracy and responsibility by regularly reviewing and updating its knowledge base to prevent misinformation and avoid unsubstantiated claims. By prioritizing these ethical guidelines, CINT creates a transformative spiritual support experience that complements traditional medical care responsibly.

VTSA

In another embodiment, a Virtual True Self Avatar (VTSA) enables immersive self-interaction and real-time biofeedback through advanced voice modulation technology. The VTSA visually represents the user within the VR environment and replicates their voice with high fidelity using AI-driven cloning techniques. By capturing vocal timbre, resonance, and speech patterns through integrated microphones and bone conduction sensors, the system synthesizes an auditory experience that mirrors the user's internal voice perception, combining air and bone conduction pathways.

During sessions, the VTSA continuously analyzes vocal parameters-including pitch variation, speaking rate, and hesitation markers-using NLP and emotion recognition algorithms. These parameters correlate with physiological and emotional states, such as stress or anxiety, inferred through deviations from predefined biomarkers. For example, a 20 Hz pitch instability may trigger cortisol-level estimates, while PPG sensors validate stress states by detecting peripheral vasoconstriction exceeding 15%. The AI then modulates the user's voice toward therapeutic targets, such as reducing speaking rate by 7-12% or stabilizing pitch to mimic parasympathetic activation, while preserving the user's vocal identity.

The modulated voice serves as auditory biofeedback, delivered via bone conduction transducers (40-120 Hz) to enhance self-regulation awareness. This approach allows users to internalize therapeutic content-such as affirmations or coping strategies-more effectively, as messages delivered in their own voice bypass cognitive resistance. Additionally, the VTSA's facial expressions animate in real-time using a first-order motion model, adjusting brow furrow intensity by 18-22% when vocal tension markers indicate anxiety.

Bone conduction hardware plays a role by replicating the user's internal voice perception, strengthening embodiment and therapeutic impact. Unlike traditional biofeedback relying on direct physiological signals, the VTSA leverages vocal behavior analysis, creating a closed-loop system where users adjust their vocalizations-and underlying statestoward healthier profiles.

Integration with the ORA/CINT architecture occurs across three layers:

Data Integration: Captures real-time vocal input and biometric data from EEG, PPG, and GSR sensors.

AI & Logic: Processes voice analysis, determines modulation parameters, and synchronizes content with VMA/VSA directives using reinforcement learning.

VR Presentation: Renders the avatar and delivers modulated voice via bone conduction or headphones, while haptic vests provide tactile feedback synchronized to stressed syllables.

This combination enhances self-acceptance, normalizes desired emotional states, and provides a scalable tool for conditions like chronic anxiety or low self-esteem. The system's blockchain-audited logs ensure HIPAA compliance, while federated learning updates models across users without compromising privacy. By merging voice cloning, AI-driven biofeedback, and immersive hardware, the VTSA introduces a paradigm shift in self-regulated therapy, offering users a mirror to refine their emotional and physiological states through their own voice.

The Cognitive and Immersive Neuro-Synergistic Technology (CINT) system integrates cutting-edge virtual reality (VR), artificial intelligence (AI), and machine learning (ML) to deliver personalized therapeutic interventions. The VR engine leverages C#scripting for dynamic interactions, avatar behavior programming, and scene management, supporting cross-platform compatibility with major headsets. Avatar implementation employs deepfake technology through the First Order Motion Model, enabling users to create or customize lifelike avatars by uploading personal images or modifying pre-trained models. Facial animations combine blend shapes for nuanced expressions (e.g., eyebrow raises, smiles) with motion capture-driven lip-syncing, while Google Cloud TTS or Amazon Polly generates adaptive voice output with adjustable tone, pitch, and accent for personalized vocal fidelity.

At its AI core, the deploy state-of-the-art models like BERT to analyze unstructured clinical notes from electronic health records (EHRs), extracting diagnoses, medications, and treatment plans through bidirectional context analysis and masked language modeling, achieving >92% F1-score after fine-tuning on medical datasets. Reinforcement learning (RL) modules, including Deep Q-Networks (DQNs), dynamically optimize therapeutic content delivery by cor relating real-time biometric feedback (e.g., heart rate variability, EEG signals) with reward functions, adjusting VR environments and avatar interactions to stabilize physiological markers like RMSSD. Recommender systems blend collaborative filtering (user preference patterns) and content-based filtering (clinical/spiritual content analysis) to tailor interventions, while Explainable AI (XAI) modules map BERT attention weights to feature importance scores, stored in blockchain-audited logs for transparency.

The system further comprises a synthetic data generation module operable to generate synthetic training data via generative adversarial networks (GANs) to address rare medical condition representation gaps. In embodiments, the synthetic data generation module is configured to receive existing training datasets and determine under-represented medical conditions within the electronic health records, and to generate additional representative data samples that mimic the statistical distribution and subtle clinical variations of such conditions. The synthetic training data is integrated into the training process of the deep neural networks responsible for avatar behavioral patterns and medical content adaptation. By leveraging GANs, the system ensures that the model is trained on an augmented dataset that includes both commonly occurring conditions and rare medical conditions, thus enhancing diagnostic accuracy and treatment relevance. The generated synthetic data is subsequently used for refining the performance of natural language processing modules in extracting clinical concepts from unstructured data and for improving the prediction capabilities of reinforcement learning algorithms responsible for optimizing avatar behavioral responses based on real-time biometric feedback. Additionally, the synthetic data generation process is performed under controlled conditions to maintain data integrity and privacy, ensuring that the generated samples do not contain personally identifiable information while accurately representing the desired medical condition features. This augmentation strategy enables the system to continuously evolve, providing more comprehensive medical guidance that is robust across a wide spectrum of clinical scenarios.

In embodiments, the system uses a reinforcement learning environment that rewards the AI agent for maintaining the user's heart rate variability (HRV) within predetermined therapeutic ranges. In one implementation, the AI controller, coupled to real-time biometric sensors, continuously monitors the user's HRV along with other physiological parameters and adjusts the therapeutic content delivered via the personalized avatar accordingly. The reinforcement learning algorithm is designed to optimize the avatar's responses in real time by establishing a reward function that assigns positive reinforcement to actions leading to HRV measurements within clinically validated ranges. For example, when the AI controller dynamically modulates the avatar's speech patterns, emotional tone, and therapeutic recommendations based on feedback from HRV and other sensor data, it receives a quantifiable reward signal proportional to the degree of HRV stabilization achieved. Conversely, actions that cause HRV to deviate from the desired therapeutic thresholds result in reduced or negative reinforcement, thereby guiding subsequent modifications in the avatar's behavior. The reward function is configured to weight HRV stabilization alongside additional biometric indicators to comprehensively evaluate the therapeutic efficacy of the delivered interventions. By iteratively adjusting its response strategies, the AI agent learns to maximize the cumulative reward over time, thereby optimizing both the selection and timing of therapeutic interventions to sustain user HRV within the targeted range and ultimately enhancing the overall efficacy of the therapeutic session.

In one embodiment, the system further comprises a module configured to deploy knowledge graph embeddings to link medical concepts with relevant spiritual analogies during joint VMA-VSA sessions. The system receives data from the natural language processing module that extracts clinical terms from electronic health records, as well as from a semantic matching module that processes spiritual texts and sacred databases. Using knowledge graph embedding techniques, discrete data nodes representing health conditions, therapeutic recommendations, and medication adherence patterns are associated with nodes representing spiritual archetypes and ritual constructs. This structured semantic mapping facilitates the generation of enriched content during combined virtual medical avatar (VMA) and virtual spiritual advisor (VSA) interactions by bridging clinical information with spiritual interpretations tailored to the user's declared preferences. In one implementation, the knowledge graph embedding module dynamically updates its associations based on real-time biometric feedback, interaction history, and user engagement metrics, thereby allowing the system to adjust therapeutic content and narrative analogies in a synchronized manner across the VMA and VSA. The integration of these embeddings permits both avatars to deliver cohesive guidance that spans the domains of medical and spiritual wellness, enhancing the overall efficacy of the therapeutic session by providing users with analogical reasoning that supports holistic healing.

In an additional embodiment, the system further comprises counterfactual explanation generators that are triggered when a user declines a treatment option recommendation. The counterfactual explanation generators analyze user-specific data, including medical records, biometric feedback, and interaction history, to construct plausible alternative scenarios in which the recommended treatment option would have been accepted. The system employs deep neural network modules integrated with transformer-based NLP architectures to generate these counterfactual explanations in natural language, thereby providing a rationale for the declined recommendation based on variations in treatment parameters such as dosage levels, administration timing, or complementary therapeutic modalities. When a treatment option is declined, the counterfactual explanation generator produces a detailed narrative that outlines potential modifications or alternative treatment pathways that lead to superior clinical efficacy, based on both historical data and simulated outcomes generated through reinforcement learning algorithms. This disclosure further contemplates that the counterfactual explanation generator interfaces with the AI controller, thereby integrating feedback from physiological and engagement metrics to refine the generated explanations. In some embodiments, the generated counterfactual explanations are recorded in a blockchain ledger using cryptographic hash functions to ensure the integrity and traceability of the explanation history, thereby providing an auditable record for both clinical decision support and patient education.

In embodiments providing interfaith content delivery, the semantic similarity matching algorithm is configured to incorporate denominational doctrinal weightings when selecting interfaith content. The algorithm analyzes user-declared spiritual preference data and compares it against sacred text databases using semantic similarity techniques enhanced by assigned weighting factors. These weighting factors reflect denominational doctrines and interpretative nuances associated with the user's indicated religious affiliations, thereby influencing the selection of content. The denominational doctrinal weightings, derived from historical doctrinal analyses or dynamically learned via machine learning techniques, assign relative importance to various doctrinal elements. As a result, the semantic similarity matching not only evaluates the linguistic and contextual similarities between user data and candidate content, but also prioritizes content that aligns with denominational doctrines, ensuring that the interfaith content delivered is both semantically relevant and doctrinally appropriate for the user.

In practice, these components work collaboratively to drive the personalized outputs of both the VMA and VSA avatars. The deep neural network and BERT architecture ensure that the avatars are informed by robust analyses of a wide spectrum of user data, while the reinforcement learning module and sensor array continuously adapt avatar behaviors in response to real-time physiological signals. The integration of federated learning safeguards data privacy and permits ongoing system refinement, and the rendering engine provides detailed, dynamic visual feedback that supports both the comprehension and efficacy of delivered healthcare interventions.

The AI-driven personalization capabilities of the system may aim to create a highly tailored and responsive virtual reality healthcare experience. By leveraging diverse data sources and advanced analytics, the system may potentially enhance the relevance, engagement, and therapeutic efficacy of the virtual environment for each user. In various embodiments, the AI Algorithm can include the protocols below.

| Area | Specifics |
| --- | --- |
| NLP | BERT, GPT-3 for sentiment analysis, text generation, intent recognition. |
| Recommender Systems | Collaborative and content-based filtering for personalized content. |
| Reinforcement Learning | Q-learning, Deep Q-Networks for dynamic VR environment adjustments. |
| Emotion Recognition | CNNs, Vision Transformers (ViTs) for real-time emotional state assessment. |
| Sensor Fusion | Combine IMU, optical, and biometric data for accurate user state assessment. |
| Real-time Processing | Optimize algorithms for low-latency VR experience (<20 ms). |
| Data Security | Encryption, anonymization, secure storage, HIPAA compliance. |

Table 5 Area NLP Recommender Systems Reinforcement Learning Emotion Recognition Specifics BERT, GPT-3 for sentiment analysis, text generation, intent recognition. Collaborative and content-based filtering for personalized content. Q-learning, Deep Q-Networks for dynamic VR environment adjustments. CNNs, Vision Transformers (ViTs) for real-time emotional state assessment. Sensor Fusion Real-time Processing Data Security Combine IMU, optical, and biometric data for accurate user state assessment. Optimize algorithms for low-latency VR experience In one embodiment, the method is executed by a computing system configured to administer adaptive therapeutic audio treatment in an augmented reality healthcare system. The method comprises receiving physiological data from a user via biometric sensors, wherein the sensors include at least an electroencephalography (EEG) module configured to capture brainwave activity and a photoplethysmography (PPG) sensor configured to detect blood volume changes in the microvascular bed of tissue. The acquired physiological data is processed in real-time by a control module that continuously monitors parameters including alpha/beta wave ratios from the EEG signals and heart rate variability (HRV) calculated from the PPG data.

In one embodiment, the therapeutic audio signals are further configured to incorporate binaural beats, wherein each ear receives a distinct audio tone generated at carrier frequencies that range between approximately 200 Hz and 900 Hz. The binaural beats are produced by delivering two tones with slightly different frequencies to the left and right auditory pathways, which in turn creates a perceptual phenomenon whereby the user experiences a third, illusory beat frequency. This dichotic auditory stimulation is designed to induce third-party neural entrainment effects, wherein neural circuits begin to synchronize with the frequency of the perceived binaural beat. The system is operable to generate these audio signals using digital signal processing techniques that ensure precise control of the carrier frequencies and interaural phase differences required for effective entrainment. Moreover, the neural entrainment effects facilitated by the binaural beats serve to enhance therapeutic outcomes by modulating neural activity, potentially improving relaxation, focus, or meditative states based on the application. The audio generation module adjusts the carrier frequencies dynamically in response to user feedback or pre-selected therapeutic profiles, ensuring that the binaural beat stimulus is optimized for individual neural response characteristics. The integration of such audio signals with the overall therapeutic framework, including biometric feedback and adaptive content delivery, provides a holistic approach to personalized therapy that leverages both auditory stimulation and real-time physiological monitoring.

In certain embodiments, the system further comprises overlaying visual neurofeedback indicators in the AR field-of-view that pulse synchronously with dominant EEG frequency bands. The system processes EEG signals to determine the user's predominant frequency components, such as those corresponding to alpha, beta, or gamma rhythms, and generates corresponding visual indicators that are superimposed on the AR display. These visual elements include dynamic icons, waveforms, or color-coded markers that modulate in pulsation rate, brightness, or size to reflect real-time changes in the dominant EEG frequency band power. The rendering engine is configured to synchronize the pulsing of the visual indicators with the detected EEG frequency so that the displayed feedback accurately represents the underlying neurophysiological state of the user. The overlay is adaptively adjusted based on sensor fusion data and can be customized in terms of transparency, position, and update frequency, ensuring it integrates seamlessly with other elements of the AR environment while remaining non-intrusive. In embodiments where the user is engaged in neurofeedback training, the pulsing indicators provide an intuitive visual cue that assists the user in modulating their cognitive or emotional state, thereby enhancing the efficacy of the therapeutic or training intervention.

In embodiments utilizing therapeutic audio signals, the Solfeggio frequencies are dynamically selected from a prioritized queue based on real-time galvanic skin response (GSR) measurements that are correlated with emotional valence classifications of the user. The prioritized queue is continuously updated as the system monitors changes in the user's emotional state, ensuring that the most therapeutically relevant frequencies are delivered at any given time. Further, the method includes the implementation of a convolutional neural network that predicts optimal audio parameter adjustments by analyzing historical engagement patterns in conjunction with real-time pupillometry data. This network utilizes the gathered data to adjust parameters such as frequency amplitude, rhythmic entrainment patterns, and interaural time differences, thereby enhancing the user's experiential responsiveness and overall therapeutic outcome.

In one embodiment, the system employs a closed-loop reinforcement learning architecture in which a deep Q-network or similar algorithm receives continuous input from one or more multimodal sensor arrays and processes real-time physiological biomarkers correlated to neuroplasticity. The architecture assigns reward signals based on measurable durable markers of neuronal reorganization, such as changes in synaptic efficacy or surrogate indicators of neurotrophic activity, which include, for example, biomarker levels inferred from extended trends in electroencephalography (EEG) or other neuroimaging modalities. The reward signals are computed by evaluating both immediate physiological responses and cumulative adaptations observed over repeated therapeutic sessions, thereby establishing a dynamic performance metric that reflects the potential for durable neuroplastic benefits. The closed-loop system then uses these reward signals to adjust operational parameters in real time, such as the timing, amplitude, and frequency of avatar-delivered therapeutic content, as well as the modulation of emotional tone and prosody in synthesized speech. By continuously updating the parameters based on the reward feedback, the system refines its intervention strategies to maximize the desired neuroplastic outcomes, effectively creating an adaptive treatment regimen that evolves with the user's physiological state and response history. The integration of durable neuroplasticity biomarkers into the reinforcement learning model ensures that the system not only responds to immediate changes in biometric data but also optimizes the therapeutic interventions over time to enhance overall treatment efficacy and promote sustained neurological improvements.

In one embodiment, the system further comprises a conversion module configured to transform unstructured spiritual journal entries into vector embeddings utilizing a paragraph-to-vector algorithm such as Doc2Vec. The conversion module receives the unstructured spiritual text and preprocesses the data by performing operations including tokenization, stop word removal, and lemmatization. The processed text is then transformed into numerical vector representations that capture the semantic content of the original spiritual entries. These generated vector embeddings are integrated with the system's repository of user spiritual preferences and sacred text databases to facilitate semantic similarity matching, thereby enhancing the accuracy of content selection for the virtual spiritual advisor (VSA) avatar. The vector embeddings serve as input for a deep neural network or other machine learning modules that further refine the selection and presentation of spiritual content based on engagement metrics and contextual relevance. This conversion process ensures that the nuanced meaning of the user's expressive spiritual journal entries is effectively captured and leveraged within the overall framework of personalized therapeutic interventions, ultimately improving the tailoring of spiritual guidance delivered during sessions.

In some embodiments, the system further comprises a module configured to generate personalized affirmation sequences through Markov chain text generation constrained by denominational doctrinal databases. In these embodiments, the Markov chain generation module couples to the user data acquisition unit and receives as input user-specific spiritual preference data along with historical interaction logs, wherein the module leverages these inputs to establish probabilistic transition models for generating affirmation sequences. The generation process utilizes pre-defined denominational doctrinal databases that store a plurality of authoritative textual passages and doctrinal affirmations related to the user-selected sphere of spiritual guidance. These databases serve as constraints by providing a curated set of tokens, phrases, and sequences that adhere to the doctrinal and theological tenets of a given denomi-nation. The Markov chain module dynamically generates affirmation sequences by traversing state transitions deter-mined by conditional probabilities, with the output sequences constrained such that only tokens or phrases present in the denominational doctrinal databases are selected. By incorporating this constrained approach, the system ensures that the generated affirmation sequences maintain consistency with established religious doctrine while providing personalized motivational or therapeutic content. The generated sequences are delivered through the virtual spiritual advisor avatar in synchrony with other therapy components, and the user's responses to these sequences are monitored in real time using the biometric sensor integrations. Additionally, user feedback and inter-action history are utilized by the system in an iterative manner to update the transition probabilities of the Markov chain module, thereby refining the personalization and doc-trinal alignment of future affirmation sequences. This adap-tive mechanism further enhances the relevance and efficacy of the generated affirmations during personalized therapeu-tic sessions.

Gamification, Incentives, and Blockchain

The system implements a gamification system that awards cryptocurrency tokens to users for completing prescribed health activities, wherein smart contract logic controls the awarding and redemption of the cryptocurrency tokens. In one embodiment, the system further comprises a gamifica-tion system that awards MetaFlux cryptocurrency tokens for user completion of VMA-prescribed health activities. Fol-lowing the provision of tailored health information and recommendations by the personalized VMA avatar, the system assigns specific health activities for the user to perform. The gamification module monitors the completion of these prescribed activities by correlating biometric data collected from sensors and user interaction history. When the system verifies that a user has satisfactorily completed the recommended activity, it issues MetaFlux tokens, which can be tracked and stored in a secure digital wallet integrated within the system. Users may earn tokens for actions such as:

Completing educational modules within the virtual envi-ronment

Achieving personalized health goals set in collaboration with virtual advisors

Consistently engaging with therapeutic content and exer-cises

Participating in virtual support groups or community activities

Demonstrating improvements in biometric measurements or health indicators

The issuance of tokens is governed by predefined criteria that include factors such as the degree of adherence to the prescribed activity, improvements in key health indices, and overall engagement with the therapeutic regimen. The AI Personalization Engine dynamically tailors challenges, quests, and reward structures to align with individual user preferences, health objectives, and historical engagement patterns (as illustrated in FIG. 2). During the VR/3D Environment & Interaction phase, users receive real-time feed-back on token earnings and progress, enhancing motivation. The token awarding process is safeguarded by blockchain-based auditing, where interaction and verification data—recorded via secure blockchain ledger mechanisms—ensure transparency and immutability of reward transactions. Blockchain specifications include:

| Feature | Specification |
|---|---|
| Layer-2 Solution | Polygon (MATIC), Arbitrum, or Optimism for scalability |
| Privacy Features | Zero-knowledge proofs (ZKPs) for anonymous transactions |
| Smart Contract Functionality | Automated MetaFlux distribution, reward allocation, and access control |
| Tokenomics | Defined supply, staking/governance models, and redemption mechanisms |
| Security Protocols | Audited contracts, multi-signature wallets, hardware wallet support, SHA-256 hashing |

The integration of MetaFlux tokens with the VMA avatar and CryptoMetaverse—a therapeutic VR ecosystem com-bining gamification, blockchain, and social interaction—creates a measurable, reward-based framework that incen-tivizes healthy behaviors. Users redeem tokens for premium VR content (e.g., immersive environments, avatar customi-zations), real-world medical services, or discounts through smart contract verification. The CryptoMetaverse further enhances engagement by enabling social features such as group challenges, collaborative health activities, and virtual community events, fostering a sense of agency and owner-ship over health journeys.

The system's blockchain module manages MetaFlux token generation, distribution, and redemption. Token trans-actions are executed via decentralized smart contracts that verify balances and thresholds, ensuring fraud-resistant exchanges. All token interactions, including spiritual inter-vention timestamps and AI recommendation updates (e.g., avatar speech patterns, emotional tone), are immutably logged using SHA-256 hashing on a blockchain ledger. The blockchain-anchored audit trail module records AI-driven parameter adjustments and associated biometric responses, enabling real-time auditing and compliance with regulatory standards.

The gamification module also awards non-fungible tokens (NFTs) for achievements like sustained gamma wave coher-ence during therapy. NFTs serve as digital credentials for therapeutic milestones and are cryptographically secured on the blockchain. Concurrently, the Real-time Monitoring & Feedback Collection phase tracks user interactions with gamified elements, informing the Adaptive Content Update process to refine reward mechanisms based on engagement analytics.

The CryptoMetaverse represents a novel convergence of therapeutic VR, blockchain economics, and gamified well-ness. Its layered architecture (per Table 4) ensures scalability and privacy while incentivizing adherence through tangible rewards. During the Review & Continuous Improvement phase, the system evaluates token efficacy, introducing new challenges and optimizing reward structures to sustain engagement. This ecosystem bridges virtual achievements with real-world health benefits, creating a transparent, immersive, and motivating framework for holistic wellness.

Meditation, Spiritual Content, and Engagement

In one embodiment, the system is further configured to include a temporal convolutional network that processes historical circadian rhythm data to predict optimal intervention timing. The temporal convolutional network analyzes sensor-derived physiological inputs collected over multiple therapeutic sessions, including indicators of circadian fluctuations, to generate timing predictions that optimize the synchronization of avatar-delivered therapeutic content with the user's natural biological rhythms. The network is trained on historical circadian rhythm datasets, which enables it to identify patterns and predict periods during which the user is most responsive to intervention. The predicted optimal intervention timing is then used to coordinate and schedule the delivery of tailored medical and/or spiritual guidance by the avatar, thereby enhancing treatment efficacy by aligning the intervention with the user's intrinsic circadian cycles. In certain embodiments the temporal convolutional network operates in conjunction with other advanced processing modules, such as deep neural networks and reinforcement learning algorithms, to provide a comprehensive adaptive framework that simultaneously optimizes content, emotional tone, and delivery timing based on both real-time and historical biometric data.

In one embodiment, the system further comprises an explainable AI (XAI) module configured to generate visualizations displaying feature importance weights for medical recommendations. The XAI module receives processed data from the NLP module and deep neural network processors responsible for analyzing electronic health records and biometric inputs. It subsequently determines the relative contribution of each input feature to the overall therapeutic recommendation generated by the system. These feature importance weights are transformed into user-understandable visual representations—such as bar graphs, heat maps, or other overlay graphics—that are integrated into the immersive 3D display output via the VR headset. The XAI visualizations update in real time to reflect any modifications in user physiological state and interaction history, thereby ensuring that the medical recommendations remain dynamically interpretable by the user.

In one embodiment, the multimodal sensors include one or more photoplethysmography (PPG) arrays configured to detect microvascular changes during guided meditation sessions. The PPG arrays comprise optical sensors with enhanced sensitivity arranged to measure variations in blood volume within superficial capillary beds and to capture the subtle hemodynamic fluctuations that occur during meditative states. The sensor data is processed by a processor that analyzes temporal changes in the photoplethysmography signals to deduce microvascular flow patterns, thereby providing an indication of the user's autonomic and cardiovascular responses during meditation. The detected microvascular changes are correlated with additional biometric signals, such as those from electroencephalography (EEG) and galvanic skin response (GSR) sensors, to generate a comprehensive profile of the user's physiological state. This profile is then used to adjust therapy-related parameters in real time, including modifying the visual and audial output of an avatar and synchronizing haptic feedback with the user's relaxation state, with the aim of optimizing the guided meditation experience. The processed PPG data further supports the system's adaptive algorithms by contributing to the calculation of cardiovascular stress indices using pulse transit time analysis, thereby enabling precise modulation of the immersive environment in accordance with the user's current level of physiological relaxation and focus.

In certain embodiments, the system comprises a blockchain ledger for recording timestamped events related to spiritual interventions and user interactions. The blockchain ledger is implemented using a proof-of-authority consensus algorithm in which validator nodes, operated by licensed spiritual counselors, verify and approve transactions. Each validator node is associated with a spiritual counselor who has met predefined licensing and accreditation requirements, thereby ensuring that only authorized entities participate in the consensus process. When a transaction, such as the recording of a spiritual intervention, is generated, it is digitally signed and transmitted to the validator nodes. Once received, the validator nodes independently verify the authenticity of the transaction by checking the digital signature and confirming that the intervention type and associated data satisfy established system criteria. Upon validation, a consensus is reached among the licensed spiritual counselors, and the transaction is appended to the blockchain ledger in an immutable manner. This proof-of-authority mechanism reduces the computational overhead typically associated with alternative consensus algorithms while providing enhanced security by leveraging the integrity and trustworthiness of the licensed spiritual counselors. In some embodiments, the system periodically updates or reassigns validator nodes to reflect the current status of licenses and ensure alignment with prevailing regulatory standards. Such dynamic management of validator node assignments further reinforces the reliability of the ledger, ensuring that all recorded interventions maintain a robust level of credibility and authority. The immutable nature of the blockchain ledger, combined with the proof-of-authority consensus, guarantees that the historical record of spiritual interventions remains tamper-proof and verifiable, thereby enhancing user confidence in the system and its ability to deliver authenticated spiritual content.

System Integration, Compliance, and Security

The method includes recording interaction data within a blockchain ledger, utilizing SHA-256 hashing for secure data management and integrity. This ensures that any modifications to the recorded data are detectable, thereby maintaining a reliable and tamper-proof record of interactions.

The system generates a blockchain-based audit trail to record user interactions and AI parameter adjustments, wherein the blockchain network securely logs the interaction data using cryptographic hashing. In one embodiment, the system further comprises generating a blockchain-based audit trail that records all VMA-user interactions to ensure HIPAA-compliant documentation. The audit trail module is operatively connected to the VMA interface and logs interaction timestamps, user inputs, system responses, and any biometric data processed during the therapeutic session. This audit log is secured using cryptographic hashing techniques, such as SHA-256, and stored in a distributed ledger to provide an immutable record of all interactions. The blockchain infrastructure is configured to allow secure, decentralized verification of logged data while maintaining the privacy and integrity of health information in accordance with HIPAA standards. The system periodically synchronizes new data entries with the distributed nodes, ensuring that each entry is time-stamped and partitioned based on the type of interaction, such as biometric monitoring events or avatar-delivered guidance. This feature not only supports regulatory compliance by providing a robust audit trail for health data but also facilitates retrospective analyses, thereby enabling continuous improvement of therapeutic interventions based on verified interaction records.

An embodiment of the present disclosure provides that anatomical models generated from medical imaging data are not only deformable to represent organ structures but are also enhanced to visually demonstrate medication mechanisms at cellular resolution. In this embodiment, particle system simulations simulate the behavior of medication particles as they interact with cellular structures. The simulation dynamically renders cellular-level interactions, thus providing a visual representation of pharmacokinetic processes such as absorption, distribution, metabolism, and excretion. The integrated particle system depicts medication particles moving through microvascular networks and interacting with target cells, offering a detailed visualization synchronized with real-time data derived from electronic health records and imaging inputs. By incorporating these particle system simulations, the system enhances the user's understanding of therapeutic impacts at a cellular scale, thereby supporting more informed decision-making in therapeutic interventions. The simulation parameters are adjusted based on real-time biometric feedback and physiological data, ensuring that the visualized mechanisms accurately reflect the current therapeutic state of the subject.

The integration of PPG sensor data into the broader biometric feedback loop enhances the precision of real-time monitoring and adjustment of the therapeutic regimen, allowing for a more individualized treatment approach. Furthermore, the system is designed to correlate PPG-derived microvascular changes with additional biometric data, enabling the development of predictive models that refine the timing and intensity of subsequent therapeutic interventions. This comprehensive approach leverages the sensitivity of PPG sensors to provide a robust measure of microvascular dynamics during exposure therapy and contributes to better therapeutic outcomes through adaptive and personalized treatment strategies.

In addition to the incorporation of stochastic resonance, the method further integrates the therapeutic audio with augmented reality exposure therapy scenarios. In this context, a real-time control algorithm adjusts the complexity of the soundscape by evaluating predictive indicators of amygdala reactivity. Specifically, biometric signals and neural activity measurements are analyzed to forecast changes in amygdala activation. These predictions are then used to dynamically modulate various parameters of the auditory environment, including the layering and density of audio elements, as well as adjustments in harmonic structures.

EXAMPLES

Aspects of the present teachings may be further understood in light of the following examples, which should not be construed as limiting the scope of the present teachings in any way.

Example 1—Examples of Clinical Use

A. Oncology Support: A Chemotherapy Patient's VR Experience

A breast cancer patient undergoing chemotherapy utilizes the ORA during and after treatment for a personalized, educational, supportive, and engaging experience.
Initial Setup:

Avatar Personalization: The patient selects a VMA representing their oncologist or creates a personalized avatar, enhancing agency.

VR Tutorial: A brief tutorial guides the patient through the VR environment, ensuring ease of navigation and optimal comfort, regardless of technical skill.

Baseline Assessment: The system assesses the patient's initial mood, anxiety, and pain levels to track VR intervention effectiveness.

Educational Module (VMA-Guided):

Treatment Explanation: The VMA explains the patient's specific cancer type, stage, and chemotherapy regimen (e.g., Epirubicin), including treatment goals, drug mechanisms, and potential side effects, using clear, age-appropriate language and visuals.

Immune System Education: The VMA clarifies the immune system's role in fighting cancer, simplifying explanations of T cells, B cells, NK cells, and macrophages.
Immersive Visualizations:

Immune Cell Visualization: The patient enters a VR environment to visualize immune cells in action, presented as engaging animations that demonstrate how they recognize and attack cancer cells. This interaction is gamified to enhance cognitive engagement and connection to the body's defenses.

Chemotherapy Agent Visualization (Epirubicin): Building on immune system understanding, the VMA explains Epirubicin's mechanism.

ORA generates a personalized 3D tumor model from the patient's MRI data. The patient sees virtual Epirubicin molecules, guided by the VMA, targeting and binding to DNA within the tumor cells.

The visualization shows the consequences of DNA damage, such as the cancer cell's inability to divide or apoptosis (programmed cell death). This reinforces that chemotherapy actively targets the cancer and reduces anxiety by visualizing the unknown. The VMA provides examples of potential physical effects, so the patient anticipates upcoming sensations.

The VMA and VSA share stories of others who underwent similar treatments to provide mental clarity and make the process seem easier.

Following chemotherapy visualization, the patient strengthens their immune system via visualization, imagining immune cells actively targeting and destroying cancer cells. The VSA provides affirmations like, "My body is strong and resilient," and "My immune system is working to protect me," empowering active participation in healing.

The VR environment shifts to a peaceful setting (e.g., forest or beach) where the patient practices deep breathing and mindfulness, releasing tension and stress. This reduces chemotherapy side effects and promotes relaxation and reduces anxiety.
Supportive Elements:

Affirmations and Solfeggio Frequencies: The VMA delivers affirmations like, "My body is strong and resilient," and "The chemotherapy is targeting the cancer cells effectively," interwoven with adaptive Solfeggio frequencies (e.g., 528 Hz for healing, and 174 Hz for pain relief) to create a calming atmosphere.

Interactive Pain Management: VR teaches and reinforces pain management techniques, guiding patients through deep breathing, progressive muscle relaxation, or guided imagery with real-time feedback. Side Effect Management Education: Dedicated modules address chemotherapy or radiation therapy side effects with practical tips and relaxation techniques. Emotional Support and Counseling: The VR environment offers access to virtual support groups or one-on-one therapy for processing emotions in a safe space. Gamification and Progress Tracking: MetaFlux and Rewards: The patient earns MetaFlux for completing educational modules and engaging with VR protocols, encouraging active participation and reinforcing learning.

Progress Tracking: ORA monitors patient progress (engagement, mood, anxiety, pain management) to personalize the experience and provide healthcare providers with valuable feedback.

Advanced Features:

Biofeedback Integration: Integrates biofeedback devices (e.g., heart rate variability sensors) to adapt the VR experience to the patient's physiological state in realtime.

Customizable Environments: Patients can customize their VR environments with calming scenes, sounds, or personalized virtual spaces.

Accessibility: Designed to be accessible to all patients, regardless of age, technical skills, or physical limitations. Multilingual support is also available.

AI Personalization: AI learns from patient data to further personalize the experience.

Remote Monitoring and Support: ORA enables remote monitoring and support, allowing providers to track progress and intervene when necessary.

EHR Integration with electronic health records facilitates data sharing and collaboration.

Oncology Care Beyond Chemotherapy:

ORA Extends Beyond Chemotherapy:

Radiation Therapy Support: The system explains the procedure and reduces anxiety via immersive environments.

Palliative Care: VR provides comfort and support for palliative care patients.

Survivorship Support: VR offers resources and guidance for patients in survivorship.

B. Weight Loss and Obesity Management: a Personalized VR Experience

This VR healthcare system helps obesity patients achieve weight loss goals and improve overall well-being through personalized content.

Customized Videos:

Educational Content: The VMA presents videos explaining the science of obesity, health risks, weight loss benefits, and practical strategies for healthy eating, exercise, and stress management, emphasizing mindset and self-efficacy.

Personalized Visualizations: The videos include a 3D model of the patient's body showing the potential impact of weight loss, visual representations of healthy food choices, animated sequences illustrating exercise benefits, and progress tracking charts. The patient visualizes their current state alongside their potential improved self with ongoing guidance.

Solfeggio Frequencies: Specific Solfeggio frequencies are selected for weight loss and well-being: 528 Hz: Promotes healing and cellular repair. 174 Hz: Reduces pain and inflammation. 741 Hz: Supports detoxification. 432 Hz: Promotes relaxation and stress reduction.

Delivery Methods: Frequencies are delivered as isochronic tones, embedded in music, or as background ambiance.

Affirmations: Explicit Affirmations: The VSA delivers affirmations promoting a positive mindset and motivation: "I am committed to achieving my weight loss goals." "I am making healthy choices every day." "I am strong and capable of overcoming challenges." "I am grateful for my body." "I am worthy of love and acceptance."

Subliminal Affirmations: Subliminal affirmations are embedded to influence the subconscious mind: "I am healthy and fit." "I am making progress."

"I am in control of my eating habits." "I am enjoying exercise." "I am feeling confident and energized."

Virtual Advisors (VMA and VSA):

The patient chooses VMA and VSA avatars, such as a nutritionist, personal trainer, or spiritual mentor.

The VMA and VSA offer interactive guidance and support, answering questions, providing encouragement, and celebrating milestones, state.

The system adapts support based on the patient's progress and emotional.

Gamification:

The system rewards healthy behaviors with MetaFlux cryptocurrency:

Completing educational modules.

Tracking food intake and exercise.

Achieving weight loss milestones.

Participating in support groups.

Gamification and cryptocurrency rewards motivate engagement.

Combining these elements creates a supportive environment that addresses the physical, mental, emotional, and spiritual factors of weight loss, empowering patients to achieve sustainable weight loss, improve their health, and cultivate a positive body image.

C. Depression

Initial Setup:

Avatar Selection: The patient selects a Virtual Mental Health Avatar (VMHA) to enhance control and connection.

Tutorial: A tutorial introduces the VR environment and therapeutic elements.

Baseline Assessment: The system assesses mood, anxiety, and energy levels to track progress.

Psychoeducation (VMHA-Guided):

Understanding Depression: The VMHA explains the biological, psychological, and social aspects of depression.

CBT Principles: Introduces CBT concepts to recognize and manage negative thoughts.

Neuroplasticity: The patient learns how the brain can rewire itself through positive engagement, reinforcing hope.

Immersive Visualizations:

Guided Emotional Processing: The patient visualizes and externalizes emotions in a safe environment, allowing for cathartic experiences.

Mood-Lifting Environments: Patients select calming nature settings to promote relaxation.

Visualization of Neurotransmitter Production: An animated sequence demonstrates how positive actions contribute to neurotransmitter balance.

Supportive Elements:

Affirmations: The VMHA Delivers Affirmations:

"I am worthy of love and happiness." "I release what no longer serves me." "Every day, I grow stronger." "I trust in my ability to heal." "I embrace peace and positivity." Solfeggio Frequencies: 396 Hz (Releasing fear and guilt) 417 Hz (Breaking negative thought patterns) 528 Hz (Healing and transformation) 639 Hz (Harmonizing relationships) 852 Hz (Enhancing intuition) Guided Mindfulness and Meditation: The VR environment includes meditation sessions focused on breath awareness.

Gamification:

Patients earn MetaFlux for completing mindfulness exercises and engaging with relaxation modules.

ORA records emotional states over time, providing visual representations of mood patterns.

The system offers daily challenges to encourage positive habit formation.

Advanced Features:

Biofeedback integration, customizable environments, multilingual support, and AI-powered personalization.

This immersive VR program fosters emotional resilience and long-term healing for patients experiencing depression.

D. Acne: Enhancing Self-Esteem and Treatment Adherence

For a patient with inflammatory acne and scarring, ORA provides customized content delivered by their chosen VMA. This content encompasses:

VMA Explanations: Clear explanations of the patient's specific acne condition, prescribed medications, their mechanisms of action, and expected benefits.

Visual Progress Anchoring:

The patient uploads a pre-treatment photo to the system.

The system also incorporates a target image, representing the patient's desired outcome: clear skin with reduced scarring. This target can be a retouched version of their own photo, or another reference image, to boost motivation The VMA and VSA consistently reference and support the patient's journey toward this visual goal.

Sound Frequencies:

528 Hz: Enhances self-confidence and self-esteem, counteracting the negative self-perception often associated with acne.

174 Hz: Reduces inflammation and supports the skin's natural healing processes.

Affirmations and Subconscious Influence: The system employs affirmations and suggestions to target the subconscious mind:

Examples of Affirmations: "My skin is healing and becoming clearer every day," "I am beautiful and confident regardless of my skin," "I am committed to my skincare routine."

Examples of Subconscious Suggestions: "Your skin is clear, radiant, and healthy," "Your body is effectively healing your skin," "You are calm, relaxed, and your skin reflects your inner peace."

E. PTSD Among Veterans: Reclaiming Peace of Mind

The Problem: Veterans with PTSD often experience intrusive memories, flashbacks, hyperarousal, and emotional numbing, significantly impacting their daily lives and reintegration into civilian society. Traditional therapies can be effective but may be limited by accessibility, stigma, and the difficulty of reliving traumatic experiences.

VR Solution: A personalized VR program designed to address the specific needs of veterans with PTSD.

Initial Setup:

Avatar Selection: The veteran selects a VMA (perhaps a fellow veteran or a trusted therapist) and personalizes it.

Safe Environment Tutorial: A gentle introduction to the VR environment, emphasizing control and safety.

Baseline Assessment: Assessment of PTSD symptoms, anxiety, and depression levels.

Psychoeducation Module (VMA-Guided):

Understanding PTSD: The VMA explains PTSD, its neurological underpinnings, and common symptoms.

Coping Mechanisms: Introduction to grounding techniques, relaxation strategies, and cognitive restructuring.

Immersive Visualizations:

Controlled Exposure Therapy: Gradual and controlled exposure to traumarelated stimuli in a safe VR environment, allowing the veteran to process memories without being overwhelmed.

Relaxation and Mindfulness Environments: Peaceful scenes (e.g., nature settings) for practicing mindfulness and stress reduction Social Reintegration Simulations: VR scenarios simulating social situations to practice coping skills and reduce anxiety related to reintegration.

Supportive Elements:

Affirmations and Solfeggio Frequencies: The VMA delivers affirmations such as, "I am safe," "I am in control," and "I am strong," interwoven with Solfeggio frequencies like 528 Hz (healing) and 396 Hz (releasing fear).

Peer Support Groups: Virtual support groups with other veterans.

Guided Meditation: Sessions focused on trauma-informed mindfulness.

Gamification and Progress Tracking

MetaFlux Rewards: Earning MetaFlux for completing modules, practicing coping skills, and attending virtual support groups.

Symptom Tracking: Monitoring PTSD symptoms and progress over time.

Advanced Features:

Biofeedback integration to monitor stress levels.

AI-powered personalization to tailor the program to individual needs.

Remote monitoring by therapists.

Expected Outcomes: Reduced PTSD symptoms, improved coping skills, decreased anxiety and depression, and enhanced social reintegration F. Mental Disease Among Homeless People: Restoring Dignity and Hope Problem: Homeless individuals often face significant mental health challenges, including schizophrenia, bipolar disorder, depression, and substance abuse. Lack of access to mental health services, stigma, and the harsh realities of homelessness exacerbate these conditions.

VR Solution: A mobile VR program designed to reach homeless individuals and provide accessible mental health support.

Initial Setup:

Trust-Building Avatar: The individual selects a VMA representing a compassionate social worker or mental health professional.

Simple Interface: Easy-to-use VR interface with minimal technical jargon

Safe Space Introduction: Emphasis on creating a safe and non-judgmental environment.

Psychoeducation Module (VMA-Guided):

Understanding Mental Illness: The VMA explains common mental illnesses, their symptoms, and available treatments in simple terms.

Destigmatization: Addressing common misconceptions and reducing stigma surrounding mental illness.

Basic Coping Skills: Teaching simple coping strategies for managing stress, anxiety, and mood swings.

Immersive Visualizations:

Calming Environments: Access to peaceful VR environments (e.g., parks, beaches) for relaxation and stress reduction.

Social Skills Training: VR scenarios simulating social interactions to practice communication and assertiveness skills.

Job Interview Simulations: Practicing job interview skills in a supportive VR environment.

Supportive Elements:

Affirmations and Solfeggio Frequencies: The VMA delivers affirmations such as, "I am worthy of help," "I am capable of change," and "I deserve a better life," paired with Solfeggio frequencies like 528 Hz (healing) and 417 Hz (breaking negative patterns).

Virtual Support Groups: Connecting individuals with virtual support groups.

Resource Navigation: Guiding individuals to local shelters, food banks, and mental health services through VR.

Gamification and Progress Tracking:

MetaFlux Incentives: Earning MetaFlux for engaging with modules and attending virtual support groups, which can be exchanged for essential items (e.g., hygiene products).

Progress Tracking: Monitoring mood, anxiety levels, and engagement with the program.

Advanced Features:

Offline access to content.

Integration with local resource databases

Partnerships with outreach programs.

Expected Outcomes: Improved mental health, reduced stigma, increased access to services, and enhanced social inclusion.

G. The Elderly in Nursing Homes: Reclaiming Joy and Dignity

Problem: Elderly individuals in nursing homes often experience social isolation, loneliness, cognitive decline, and a lack of meaningful activities. This can lead to depression, anxiety, and a reduced quality of life VR Solution: A VR program designed to enhance the well-being of elderly residents in nursing homes.

1. Initial Setup:

Familiar Avatar: The resident selects a VMA representing a friendly companion or a younger version of themselves.

Simple Interface: Easy-to-use VR interface with large buttons and clear instructions.

Comfortable Setting: Introduction to a calming and familiar VR environment.

2. Cognitive Stimulation Module (VMA-Guided):

Memory Recall Exercises: VR games and activities designed to stimulate memory and cognitive function.

Virtual Travel: Immersive virtual tours of familiar places or dream destinations Creative Expression: Opportunities for virtual painting, music creation, and storytelling.

3. Social Engagement Module:

Virtual Social Gatherings: VR environments simulating social gatherings (e.g., parties, concerts) to reduce loneliness and isolation.

Family Connection: Opportunities for virtual visits with family members who live far away.

4. Supportive Elements:

Affirmations and Solfeggio Frequencies: The VMA delivers affirmations such as, "I am loved," "I am valued," and "I have a purpose," paired with Solfeggio frequencies like 528 Hz (healing) and 639 Hz (harmonizing relationships).

Reminiscence Therapy: Guided VR sessions focused on recalling positive memories and life experiences.

Spiritual Support: Access to virtual religious services or spiritual guidance.

5. Gamification and Progress Tracking:

MetaFlux Rewards: Earning MetaFlux for participating in activities and engaging with other residents.

Mood Tracking: Monitoring mood and engagement levels. [0271]6. Advanced Features:

Integration with existing nursing home activity schedules.

Customizable content based on resident preferences.

Remote monitoring by caregivers.

H. Additional Indications

In addition to the above listed indications, other potential applications of ORA include:

Chronic Pain Management:

Application: Utilize VR to deliver relaxation techniques, mindfulness exercises, and guided visualizations for pain distraction and relief.

Integration: Combine visual content with specific Solfeggio frequencies (e.g., 174 Hz for pain relief) to promote relaxation and healing pain.

Example Conditions: Arthritis, fibromyalgia, migraines, and post-surgical

Pediatric Care: Application: Engage children with gamified educational content explaining their condition and treatments (e.g., asthma, diabetes, or leukemia).

Integration: Use cartoon avatars and fun, interactive environments to minimize fear and promote understanding.

Example Use Case: Preparing children for vaccinations or surgeries.

Rehabilitation for Stroke and Neurological Disorders:

Application: Assist stroke patients with motor skill recovery using interactive exercises in VR that stimulate neuroplasticity.

Integration: Tailor experiences with feedback loops to track progress and adapt therapy, supported by motivational affirmations.

Example Conditions: Stroke rehabilitation, traumatic brain injuries, and neurodegenerative diseases like Parkinson's.

Mental Health Therapy:

Application: Provide exposure therapy for phobias, guided VR meditations for stress reduction, and affirmations for building resilience.

Integration: Include sound frequencies (e.g., 432 Hz for relaxation) and content addressing anxiety, PTSD, or bipolar disorder.

Example Use Cases: Phobia desensitization (e.g., fear of flying), social anxiety therapy, and PTSD recovery.

Post-Surgical Recovery:

Application: Facilitate faster recovery by educating patients on the healing process and providing immersive relaxation environments.

Accelerated Healing and Self-Actualization: The synergistic blend of personalized education, emotional support, adaptive therapy, and visualization tools empowers patients to actively participate in their healing journey, fostering a sense of self efficacy and promoting faster recovery Integration: Use visualizations of internal healing processes and sound frequencies (e.g., 528 Hz for cellular repair).

Example Procedures: Orthopedic surgeries, organ transplants, or cesarean sections.

Weight Loss and Metabolic Disorders:

Application: Educate patients on metabolic processes and offer motivational tools for diet adherence and exercise routines Integration: Combine educational modules with positive affirmations and VR-based fitness challenges.

Example Conditions: Obesity, diabetes, and metabolic syndrome.

Cardiac Rehabilitation:

Application: Provide immersive stress management exercises and educational content about heart health and lifestyle changes.

Integration: Use guided visualizations of improved cardiovascular function with affirmations like "My heart is strong and healthy."

Example Use Cases: Post-heart attack recovery and managing hypertension.

Sleep Disorders:

Application: Offer VR-guided sleep hygiene routines, mindfulness exercises, and calming environments to improve sleep quality.

Integration: Incorporate sound frequencies (e.g., 396 Hz to release stress) to enhance relaxation.

Example Use Cases: Insomnia, sleep apnea education, and circadian rhythm disorders.

Geriatric Care:

Application: Engage older adults with VR exercises for cognitive stimulation, memory improvement, and emotional well-being.

Integration: Tailor affirmations to reinforce self-worth and reduce feelings of isolation.

Example Use Cases: Alzheimer's therapy, combating loneliness, and maintaining mobility.

Smoking Cessation:

Application: Illustrate the long-term benefits of quitting smoking and visualize healing in the lungs.

Integration: Combine 741 Hz for detoxification with affirmations like "I am free from smoking."

Example Use Case: Support groups or individual cessation programs.

Sports Rehabilitation and Performance:

Application: Support athletes recovering from injuries with guided VR exercises that rebuild strength and coordination.

Integration: Combine affirmations with visuals of successful performance to rebuild confidence.

Example Conditions: ACL recovery, tendonitis, or stress fractures.

Preoperative Anxiety Reduction:

Application: Prepare patients for surgery by explaining procedures in an immersive, calming way.

Integration: Use VR relaxation techniques and affirmations to reduce stress pre-surgery.

Example Procedures: Dental surgery, orthopedic procedures, or cosmetic surgeries.

Post-Traumatic Rehabilitation:

Application: Help individuals recover from physical trauma through guided visualizations and personalized encouragement.

Integration: Include calming frequencies (e.g., 396 Hz for releasing fear) and adaptive exercises.

Example Use Cases: Recovery after car accidents or military injuries.

Pregnancy and Childbirth Support:

Application: Educate pregnant women about labor and delivery, while providing VR-based relaxation techniques for pain management.

Integration: Include affirmations for confidence and sound frequencies for calming during contractions.

Example Use Cases: Prenatal education, labor preparation, and postpartum recovery.

Infectious Disease Management:

Application: Educate patients on infection prevention and self-care techniques for conditions like COVID-19.

Integration: Combine affirmations for immune strength with tailored VR hygiene tutorials.

Example Use Cases: Long COVID rehabilitation and flu prevention campaigns.

Dental Procedures:

Application: Reduce dental anxiety by simulating procedures in VR and providing calming exercises during treatment.

Integration: Use affirmations and gentle sound frequencies for relaxation.

Example Procedures: Root canals, extractions, or orthodontics.

Veterans' Health:

Application: Address PTSD, chronic pain, or physical rehabilitation needs in veteran populations.

Integration: Use tailored content focusing on resilience and reintegration into civilian life.

Example Use Cases: Mental health therapy for combat veterans and injury recovery.

OTHER EMBODIMENTS

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Incorporated herein by reference shall include the following references:

Bandura, A. (1977). Social learning theory. Englewood Cliffs, NJ: Prentice

Cialdini, R. B. (2009). Influence: Science and practice. Boston: Pearson Education.

Kabat-Zinn, J. (2013). Full catastrophe living: Using the wisdom of your body and mind to face stress, pain, and illness. New York: Bantam Books.

Koenig, H. G. (2012). Spirituality in patient care: Why, how, when, and what. Templeton Foundation Press.

Masters, K. S., & Spielmans, G. I. (2007). Prayer and health: Review, metaanalysis, and research agenda. Journal of Behavioral Medicine, 30(4), 329-338.

Mittelstadt, B. D., Allo, P., Taddeo, M., Wachter, S., & Floridi, L. (2016). The ethics of algorithms: Mapping the debate. Big Data & Society, 3(2).

Norcross, J. C. (2011). Psychotherapy relationships that work: Therapist contributions and responsiveness to patients. Oxford University Press.

Pargament, K. I. (1997). The psychology of religion and coping: Theory, research, practice. Guilford Press.

Pargament, K. I. (2013). Spirituality integrated psychotherapy: Understanding and addressing the sacred. Guilford Press.

Shapiro, S. L. (2009). The integration of mindfulness and psychology.

Clinical Studies on VR Efficacy

Riva, G., & Wiederhold, B. K. (2020), The new dawn of virtual reality in health care: Medical simulation and experiential interface, Annual Review of Cyber Therapy and Telemedicine, 18, 3-7.

Li, A., Montano, Z., Chen, V. J., & Gold, J. I. (2011), Virtual reality and pain management: Current trends and future directions, Pain Management, 1(2), 147-157.-61-Docket No.: TABI-01-PRV1

Garrett, B., Taverner, T., & McDade, P. (2017), Virtual reality as an adjunct home therapy in chronic pain management, JMIR Medical Informatics, 5(2), e11.

Fodor, L. A., Cotet, C. D., Cuijpers, P., et al. (2018), The efficacy of VRbased interventions for symptoms of anxiety and depression, Journal of Affective Disorders, 239, 142-149.

Naghdi, L., Ahonen, H., Macario, P., & Bartel, L. (2015), The effect of low frequency sound stimulation on fibromyalgia patients, Pain Research and Management, 20(1), e21-e27. DOI: 10.1155/2015/375174

Dos Santos, A. C., de Abreu, M. S., de Mello, G. P., et al. (2023), Solfeggiofrequency music exposure reverses cognitive deficits in zebrafish, Behavioural Brain Research, 450, 114461. DOI: 10.1016/j.bbr.2023.114461

Vincent, C., Eberts, M., Naik, T., et al. (2021), Provider experiences of virtual reality in clinical treatment, PLOS ONE, 16(10), e0259364. DOI: 10.1371/journal.pone.0259364

Neuroplasticity & Brainwave Entrainment

Merzenich, M. M., et al. (1983), Somatosensory cortical map changes following digit amputation, Journal of Comparative Neurology, 224(4), 591-605.

Doidge, N. (2007), The Brain That Changes Itself, Penguin Books.

Padmanabhan, R., Ali, A., Longe, O., et al. (2005), Binaural beat effects on EEG and heart rate, Applied Psychophysiology and Biofeedback, 30(3), 291-300. Journal of C References Related to Gamification Bandura, A. (1977). Social learning theory. Prentice-Hall.

Deci, E. L., & Ryan, R. M. (1985). Intrinsic motivation and self-determination in human behavior. Plenum.

Landers, R. N. (2014). Developing a theory of gamified learning: Linking serious games and gamification of learning. Simulation & Gaming, 45(6), 752-768.

Locke, E. A., & Latham, G. P. (2002). A theory of goal setting & task performance. Prentice-Hall, Inc.

Nakamoto, S. (2008). Bitcoin: A peer-to-peer electronic cash system.

References related to affirmations and subconscious cues for enhanced

Doidge, N. (2007). The brain that changes itself: Stories of personal triumph from the frontiers of brain science. Viking.

Lipton, B. H. (2005). The biology of belief: Unleashing the power of consciousness, matter, and miracles. Hay House.

Pert, C. B. (1997). Molecules of emotion: The science behind mind-body medicine. Scribner.

Trappl, R. (Ed.). (2016). A construction manual for robots' ethical systems: Why they are needed and how they could be built. Springer. Weinberger, J. (1992). Common processes underlying psychotherapy. Clinical Psychology Review, 12(5), 479-498.

Wood, J. V., Perunovic, W. Q. E., & Lee, J. W. (2009). Positive Self Statements: Power for Some, Peril for Others. Psychological Science, 20(7), 860-866.

The invention claimed is:

1. A computer-implemented method for administering adaptive therapeutic audio treatment in an augmented reality (AR) healthcare system, comprising:

receiving user physiological data via biometric sensors including at least electroencephalography (EEG) and photoplethysmography (PPG);

generating personalized therapeutic audio signals comprising Solfeggio frequencies combined with isochronic tones; and rendering said audio signals spatially within an AR environment via bone conduction transducers integrated into AR glasses;

monitoring real-time alpha/beta wave ratios and heart rate variability (HRV) during audio delivery; and dynamically adjusting frequency amplitudes, interaural time differences, and rhythmic entrainment patterns based on changes in said physiological data.

2. The method of claim 1, wherein the therapeutic audio signals incorporate binaural beats with carrier frequencies between 200-900 Hz, generating third-party neural entrainment effects via dichotic auditory stimulation.

3. The method of claim 1, further comprising overlaying visual neurofeedback indicators in the AR field-of-view that pulse synchronously with dominant EEG frequency bands.

4. The method of claim 1, wherein the Solfeggio frequencies are dynamically selected from a prioritized queue based on galvanic skin response (GSR) measurements correlated with emotional valence classifications.

5. The method of claim 1, wherein the AR environment contextualizes audio therapy through 3D visualizations of neural oscillatory activity mapped to corresponding treatment frequencies.

6. The method of claim 1, further comprising triggering haptic feedback patterns in wearable devices phase-locked to theta and gamma brainwave synchronization events.

7. The method of claim 1, wherein the isochronic tones are dynamically modulated to maintain a phase relationship with dominant respiratory sinus arrhythmia rhythms.

8. The method of claim 1, further integrating the therapeutic audio with AR-guided mindfulness exercises, wherein spatialized voice prompts adapt cadence inversely proportional to real-time cortisol level estimates.

9. The method of claim 1, wherein the system cross-references a pharmaceutical database to audibly highlight potential interactions between current medications and specific frequency ranges.

10. The method of claim 1, further comprising generating blockchain-anchored treatment logs recording all audio parameter adjustments and associated biometric responses for regulatory compliance.

11. The method of claim 1, wherein the AR glasses implement beamforming techniques to isolate therapeutic audio signals from environmental noise.

12. The method of claim 1, further utilizing a generative adversarial network (GAN) to synthesize personalized binaural compositions based on music preference profiles and stress biomarker patterns.

13. The method of claim 1, wherein the system modulates interaural level differences to create virtual sound source movements synchronized with guided visual focus exercises.

14. The method of claim 1, further implementing differential privacy filters on raw EEG data during federated learning updates to audio personalization models.

15. The method of claim 1, wherein the AR environment renders real-time audiographic representations of autonomic nervous system balance using particle systems responsive to HRV metrics.

16. The method of claim 1, further comprising a gamification system awarding non-fungible tokens (NFTs) for achieving sustained gamma wave coherence during therapeutic sessions.

17. The method of claim 1, wherein the audio signals incorporate stochastic resonance patterns calibrated to enhance signal detection in auditory processing pathways.

18. The method of claim 1, wherein the system implements a closed-loop reinforcement learning architecture optimizing reward signals based on long-term neuroplasticity biomarkers.

19. A computer-implemented method for operating a virtual spiritual advisor (VSA) system, comprising:

receiving spiritual preference data comprising at least one user-selected spiritual archetype through a graphical user interface;

generating a deepfake-animated VSA avatar in real-time using a graphics processing unit (GPU) implementing first-order motion models on reference images stored in non-transitory memory;

outputting therapeutic audio frequencies through bone conduction headphones while simultaneously displaying the VSA avatar via a virtual reality headset;

processing electroencephalogram (EEG) signals through Butterworth filters to detect alpha/beta wave ratios using a biosignal processing pipeline;

modulating the VSA avatar's vocal tract parameters through a Griffin-Lim vocoder based on heart rate variability metrics derived from photoplethysmography (PPG) sensor data;

synchronizing haptic feedback patterns in a wearable vest with guided meditation sequences using wireless protocols; and recording interaction timestamps and spiritual intervention types in a blockchain ledger.

20. The method of claim 19, further comprising training a bidirectional encoder representations from transformers (BERT) model on tokenized sacred texts using byte-pair encoding, wherein the deepfake animation utilizes facial landmark detection with facial mesh warping.

\* \* \* \* \*